United States Patent
Koga et al.

(10) Patent No.: US 12,279,890 B2
(45) Date of Patent: Apr. 22, 2025

(54) PRESSURE-SENSITIVE SENSOR, MAT SYSTEM USING PRESSURE-SENSITIVE SENSOR, AND METHOD FOR MANUFACTURING PRESSURE-SENSITIVE SENSOR

(71) Applicant: TAKANO CO., LTD., Nagano (JP)

(72) Inventors: Yoshiro Koga, Kamiina-gun (JP); Takamichi Ito, Kamiina-gun (JP)

(73) Assignee: TAKANO CO., LTD., Nagano (JP)

( * ) Notice: Subject to any disclaimer, the term of this patent is extended or adjusted under 35 U.S.C. 154(b) by 1197 days.

(21) Appl. No.: 17/054,947

(22) PCT Filed: Mar. 18, 2019

(86) PCT No.: PCT/JP2019/011086
§ 371 (c)(1),
(2) Date: Nov. 12, 2020

(87) PCT Pub. No.: WO2020/012719
PCT Pub. Date: Jan. 16, 2020

(65) Prior Publication Data
US 2021/0244333 A1    Aug. 12, 2021

(30) Foreign Application Priority Data

Jul. 9, 2018   (JP) ................................ 2018-130207
Jul. 9, 2018   (JP) ................................ 2018-130209
(Continued)

(51) Int. Cl.
*G01L 5/1623*   (2020.01)
*A61B 5/00*   (2006.01)
(Continued)

(52) U.S. Cl.
CPC .......... *A61B 5/6892* (2013.01); *A61B 5/1036* (2013.01); *A61B 5/27* (2021.01);
(Continued)

(58) Field of Classification Search
CPC . A61B 5/0205; A61B 5/02444; A61B 5/1036; A61B 5/1116; A61B 5/27;
(Continued)

(56) References Cited

U.S. PATENT DOCUMENTS 7,112,755 B2   9/2006   Kitano et al.
8,966,997 B2   3/2015   Taylor
(Continued)

FOREIGN PATENT DOCUMENTS

| JP | 3882172 B2 | 2/2007 |
| JP | 4780058 B2 | 9/2011 |
| JP | 2014-108134 A | 6/2014 |

OTHER PUBLICATIONS

Japanese Office Action for Japanese Application No. 2018-139941, dated Apr. 20, 2021, with English translation.
(Continued)

*Primary Examiner* — Alexander A Mercado
(74) *Attorney, Agent, or Firm* — Birch, Stewart, Kolasch & Birch, LLP

(57) ABSTRACT

A pressure-sensitive sensor includes a plurality of first-electrode cloths arranged at a first-interval on a first-surface of a conductive cloth and a plurality of second-electrode cloths arranged at a second-interval on a second-surface of the conductive cloth in a direction intersecting that of the first-electrode cloths. Areas of intersection between the first-electrode cloths and the second-electrode cloths are formed to have a matrix structure, first-conductive particles are applied to coat the conductive cloth, and second-conductive particles having greater electrical conductivity than
(Continued)

the first-conductive particles are applied to coat the first-electrode cloths and the second-electrode cloths.

14 Claims, 25 Drawing Sheets

(30) Foreign Application Priority Data

| | | |
|---|---|---|
| Jul. 9, 2018 | (JP) | 2018-130215 |
| Jul. 26, 2018 | (JP) | 2018-139941 |
| Jul. 30, 2018 | (JP) | 2018-142825 |

(51) Int. Cl.
    *A61B 5/103*     (2006.01)
    *A61B 5/27*     (2021.01)
    *G01L 1/00*     (2006.01)
    *G01L 5/00*     (2006.01)

(52) U.S. Cl.
    CPC ............... *G01L 1/00* (2013.01); *G01L 5/00* (2013.01); *G01L 5/1623* (2020.01); *A61B 2562/0247* (2013.01); *A61B 2562/125* (2013.01)

(58) Field of Classification Search
    CPC .......... A61B 5/6892; A61B 2562/0247; A61B 2562/046; A61B 2562/125; G01L 1/00; G01L 1/20; G01L 5/00; G01L 5/1623
    See application file for complete search history.

(56) References Cited

U.S. PATENT DOCUMENTS

| | | | | |
|---|---|---|---|---|
| 11,534,929 | B2* | 12/2022 | Natori | G01L 1/16 |
| 2012/0323501 | A1* | 12/2012 | Sarrafzadeh | G01L 1/18 |
| | | | | 702/41 |
| 2018/0171514 | A1* | 6/2018 | Cobanoglu | G01K 7/003 |
| 2019/0234817 | A1* | 8/2019 | Sun | A61B 5/0536 |
| 2019/0362866 | A1* | 11/2019 | Lussey | H01B 1/24 |
| 2020/0333276 | A1* | 10/2020 | Ikoma | G01M 3/18 |
| 2021/0270691 | A1* | 9/2021 | Shah | E04D 5/10 |

OTHER PUBLICATIONS

International Search Report issued in PCT/JP2019/011086 (PCT/ISA/210), dated Apr. 23, 2019.

* cited by examiner

PRESSURE-SENSITIVE SENSOR, MAT SYSTEM USING PRESSURE-SENSITIVE SENSOR, AND METHOD FOR MANUFACTURING PRESSURE-SENSITIVE SENSOR

TECHNICAL FIELD

The present invention relates to a pressure-sensitive sensor for measuring biological information.

BACKGROUND ART

These days, pressure-sensitive sensors have been used to measure pressure distribution of a sleeping posture on a bed or a sitting posture in a chair, etc. as biological information so as to perform care, enhance good health, etc. In case that the pressure-sensitive sensor is brought into contact with a human body to measure biological information, it is necessary to use the pressure-sensitive sensor which has flexibility with little uncomfortable feeling, to have a large size corresponding to the human body and to be capable of performing wide-range pressure distribution measurement.

Conventionally, a pressure-sensitive sensor, which comprises: a cloth member being constituted by a conductive member in which a cloth is coated with a mixture of conductive high polymer and binder resin; and a plurality of conductive linear members being composed of fibers coated with conductive high polymer and being disposed to contact both surfaces of a conductive surface of the cloth member wherein a plurality of the conductive linear members arranged almost in parallel on the front surface of the conductive surface are arranged to be almost orthogonal to a plurality of the conductive linear members arranged almost in parallel on the rear surface of the conductive surface, has been proposed (see Patent Literature 1: Japanese Laid-open Patent Publication No. 2014-108134).

Further, a pressure-sensitive cloth sheet, which has a first-layer sheet, a second-layer sheet and a third-layer sheet and in which the first-layer sheet and the third-layer sheet have conductive paths coated with conductive particles and arranged at a predetermined interval, an orientation direction of the conductive paths of the first-layer sheet is a crosswise direction with respect to an orientation direction of the conductive paths of the third-layer sheet and an electric characteristic of the second-sheet is varied by a pressurizing force, has been proposed (see Patent Literature 2: Specification of U.S. Pat. No. 8,966,997).

CITATION LIST

Patent Literature

Patent Literature 1: Japanese Laid-open Patent Publication No. 2014-108134
Patent Literature 2: Specification of U.S. Pat. No. 8,966,997

SUMMARY OF INVENTION

Technical Problem

In the pressure-sensitive sensor disclosed in Patent Literature 1, a pressurizing force is measured in a state where the conductive cloth member and the conductive linear members point-contact or line-contact each other; in the measurement in the point-contact state or the line-contact state, a resistance value is greater than that measured in a surface-contact state, and the point- or linear-contact state is unstable and fluctuation of the resistance value becomes greater.

In the pressure-sensitive sheet disclosed in Patent Literature 2, cloths are plated with conductive noble metal particles, so a material cost must be highly increased.

For example, in case of plating the cloths with conductive noble metal particles, it is necessary to perform treatments of removing oil content from the cloths, applying a catalytic agent, activating surfaces of the cloths, etc. as pretreatments, so treatment steps must be complex, and there is concern that the chemical treatments damage the cloths. Further, sizes of the cloths are restricted by a size of plating facility, so it is difficult to manufacture the pressure-sensitive sheet having a large size.

Solution to Problem

The present invention has been invented under the above described circumstances, an object is to provide a pressure-sensitive sensor capable of stably measuring a pressurizing force with utilizing flexibility of cloths, having sizes capable of performing wide-range pressure distribution measurement without being restricted by a size of facility, e.g., plating facility, and increasing productivity with restraining a material cost.

The present invention has been accomplished under the solutions as disclosed below.

The pressure-sensitive sensor of the present invention comprises: a conductive cloth; a first-electrode cloth being provided on a first-surface of the conductive cloth; and a second-electrode cloth being provided on a second-surface of the conductive cloth, wherein a plurality of first-electrodes are formed on the first-electrode cloth and arranged at a first-interval, a plurality of second-electrodes are formed on the second-electrode cloth and arranged at a second-interval, the second-electrodes are arranged in a direction intersecting that of the first-electrodes, and areas of intersection between the first-electrode electrodes and the second-electrodes are formed so as to have a matrix structure, or the pressure-sensitive sensor comprises: a conductive cloth; a plurality of first-electrode cloths being arranged at a first-interval on a first-surface of the conductive cloth; and a plurality of second-conductive cloths being arranged at a second-interval on a second-surface of the conductive cloth in a direction intersecting that of the first-electrode cloths, wherein areas of intersection between the first-electrode cloths and the second-electrode cloths are formed so as to have a matrix structure, first-conductive particles are applied to coat the conductive cloth, second-conductive particles having greater electrical conductivity than the first-conductive particles are applied to coat the first-electrode cloth or cloths and the second-electrode cloth or cloths, and the first-conductive particles are composed of conductive carbon black.

With the above described structure, the conductive carbon black is applied to coat the cloth, so that the sensor has flexibility with little uncomfortable feeling for a human body, can have a large size corresponding to the human body without being restricted by a size of facility, e.g., plating facility, can perform wide-range pressure distribution measurement and can stably measure a pressurizing force in a surface-contact state. Further, the conductive carbon black has a branch structure, reduces a resistance value by tunnel effect and can be obtained with at a lower price than noble metals and conductive high polymer compounds, so that high productivity can be enabled with restraining the material cost. A resistance value of the conductive cloth is greater than that of the first-electrode cloth or cloths and the second-electrode cloth or cloths, so that fluctuation of resistance values according to measurement positions and cross talk can be reduced. Further, the areas of intersection are formed so as to have the matrix structure, so that accuracy of measuring the pressurizing force can be improved in each of the areas of intersection.

The method of manufacturing a pressure-sensitive sensor of the present invention comprises: a conductive cloth; a first-electrode cloth being provided on a first-surface of the conductive cloth; and a second-electrode cloth being provided on a second-surface of the conductive cloth, wherein a plurality of first-electrodes are formed on the first-electrode cloth and arranged at a first-interval, a plurality of second-electrodes are formed on the second-electrode cloth and arranged at a second-interval, the second-electrodes are arranged in a direction intersecting that of the first-electrodes, and areas of intersection between the first-electrode electrodes and the second-electrodes are formed so as to have a matrix structure, or the method of manufacturing a pressure-sensitive sensor comprises: a conductive cloth; a plurality of first-electrode cloths being arranged at a first-interval on a first-surface of the conductive cloth; and a plurality of second-conductive cloths being arranged at a second-interval on a second-surface of the conductive cloth in a direction intersecting that of the first-electrode cloths, wherein areas of intersection between the first-electrode cloths and second-electrode cloths are formed so as to have a matrix structure, the method comprises: a step of forming the conductive cloth by applying a dispersion liquid of first-conductive particles to coat a first-base cloth so as to form the conductive cloth; and a step of forming electrode cloths by applying a dispersion liquid of second-conductive particles having greater electrical conductivity than the first-conductive particles to coat second-base cloths so as to form the first-electrode cloth or cloths and the second-electrode cloth or cloths, and the first-conductive particles are composed of conductive carbon black. With this method, the pressure-sensitive sensor can be manufactured, by simple coating steps, without being restricted by a size of facility, e.g., plating facility. Further, the conductive carbon black can be obtained with at a lower price than noble metals and conductive high polymer compounds, so that high productivity can be enabled with restraining the material cost.

Preferably, the conductive carbon black is composed of one or more out of ketjenblack, acetyleneblack, channelblack and furnaceblack, each of which has an average particle diameter of the primary particles of 100 nm or less. With this structure, a required resistance value can be obtained by adding a small quantity thereof, so that the conductive cloth having superior abrasion resistance and superior flexibility can be provided.

Preferably, the pressure-sensitive sensor comprises: the first-electrode cloth being provided on the first-surface of the conductive cloth; the second-electrode cloth being provided on the second-surface of the conductive cloth: and sewing threads, a plurality of the first-electrodes are formed on the first-electrode cloth and arranged at the first-interval, a plurality of the second-electrodes are formed on the second-electrode cloth and arranged at the second-interval, the second-electrodes are arranged in a direction intersecting that of the first-electrodes, and the areas of intersection between the first-electrode electrodes and the second-electrodes are formed so as to have the matrix structure, or the pressure-sensitive sensor comprises: the conductive cloth; a plurality of the first-electrode cloths being arranged at the first-interval on the first-surface of the conductive cloth; a plurality of the second-conductive cloths being arranged at the second-interval on the second-surface of the conductive cloth in a direction intersecting that of the first-electrode cloths; and sewing threads, and the areas of intersection between the first-electrode electrodes and the second-electrodes are formed so as to have the matrix structure, and the first-electrode cloth or cloths are sewn to the conductive cloth with the sewing threads, and the second-electrode cloth or cloths are sewn to the conductive cloth with the sewing threads.

With the above described structure, the electrode cloths are sewn to and integrated with the conductive cloth, so that displacement of measuring areas can be prevented, and the pressurizing force can be stably measured with utilizing the flexibility of the cloths. The size capable of performing wide-range pressure distribution measurement can be enabled. The pressurizing force can be stably measured in the surface-contact state, and productivity can be highly increased with restraining the material cost. Further, boundaries of the areas of intersection can be stabilized by sewing, so that accuracy of measuring the pressurizing force can be improved in each of the areas of intersection.

Preferably, the pressure-sensitive sensor comprises: the first-electrode cloth being provided on the first-surface of the conductive cloth; and the second-electrode cloth being provided on the second-surface of the conductive cloths, the [m] number of first-electrodes are formed on the first-electrode cloth and arranged at the first-interval, the [n] number of second-electrodes are formed on the second-electrode cloth and arranged at the second-interval, the second-electrodes are arranged in the direction intersecting that of the first-electrodes, and the areas of intersection between the first-electrode electrodes and the second-electrodes are formed so as to have the matrix structure, or the pressure-sensitive sensor comprises: the [m] number of first-electrode cloths being arranged at the first-interval on the first-surface of the conductive cloth; the [n] number of second-conductive cloths being arranged at the second-interval on the second-surface of the conductive cloth in the direction intersecting that of the first-electrode cloths, and the areas of intersection between the first-electrode cloths and the second-electrode cloths are formed so as to have the matrix structure, and a resistance value Re [Ω], which is an average resistance value of the two areas of intersection longitudinally adjacent to each other in the longitudinal direction, with respect to an average resistance value Rc [Ω] of the areas of intersection in a thickness direction, in a state where an external force of 50 [mmHg] is applied in a compaction direction to move the first-electrode cloth or cloths and the second-electrode cloth or cloths close to each other, satisfies the following Formula (1)

Formula (1)

$$1 < Re < (Rc/(m+n)) \tag{1}$$

With the above described structure, the pressurizing force can be stably measured with utilizing the flexibility of the cloths, the size capable of performing wide-range pressure distribution measurement can be enabled, and productivity can be highly increased with restraining the material cost. Further, surface resistances of the belt-shaped electrodes provided on an upper side and a lower side of the conductive cloth are more than two orders of value smaller than a surface resistance of the conductive cloth, so that accuracy of measuring the pressurizing force can be improved in each of the areas of intersection.

Preferably, a pressure-containing member for containing prescribed pressure in the compaction direction is provided to at least one of the areas of intersection. With this structure, the pressure-containing member capable of holding at the prescribed pressure in the compaction direction can be provided; and correcting or calibrating abnormalities, e.g., deformation of the pressure-sensitive parts caused by compression permanent set, contact resistances between the electrodes and the pressure-sensitive parts, variation of use environment such as temperature, humidity, water-invasion to the pressure-sensitive parts, can be easily performed, with maintaining and improving reproducibility of the sensed value, by treating the sensed pressure value of the pressure-containing members as standards.

Preferably, the pressure-containing member is provided to at least one of the areas of intersection located at four corners, and correcting or calibrating pressure distribution at a position different from that of the pressure-containing member is performed on the basis of a sensed pressure value at the position of the pressure-containing member. With this structure, the pressure-containing member is provided to a position displaced from a center of the part contacting the human body, so that measuring biological information can be performed with no difficulty even if the pressure-containing member is thick.

Preferably, a plurality of the pressure-containing members are provided to a plurality of the areas of intersection, and pressures of the pressure-containing members at respective positions are different from each other. With this structure, the pressures of the pressure-containing members are made difference, for example, around a lower limit and around an upper limit of a pressurizing force range of 10-200 [mmHg], so that accuracy of correction or calibration can be improved within a use range of the pressurizing force.

Preferably, the pressure-containing member has an elastic part capable of applying prescribed pressure in the compaction direction. With this structure, the pressurizing force can be easily adjusted to a desired value.

The mat system of the present invention comprises: a mat; a magnetic field generating sheet having a plurality of magnetic field generating parts matrically arranged on a body-side of the mat; the pressure-sensitive sensor having a plurality of pressure-sensitive parts matrically arranged, on the body-side of the magnetic field generating sheet, to correspond to the field generating parts; and a controller for controlling the positions of the magnetic field generating parts to generate magnetic fields and timing of generating magnetic fields according to pressure distribution of the pressure-sensitive parts. With this structure, the positions of the magnetic field generating parts to generate magnetic fields and timing of generating magnetic fields according to the pressure distribution of the pressure-sensitive parts can be controlled, so that a blood flow of the human body can be accelerated with low noise, and controlling the wide-range pressure distribution measurement corresponding to the human body can be performed while utilizing the flexibility with little uncomfortable feeling for the human body.

Preferably, the magnetic field generating parts are electromagnetic coils. With this structure, in addition to the positions of magnetic fields generated by exciting the electromagnetic coils and timing for generating magnetic fields, magnetic field intensities can be controlled; especially, the blood flow of the human body can be accelerated by moving the magnetic fields within a region in which the pressure is made high for a long time.

Preferably, the magnetic field generating sheet has a multilayer wiring substrate, and the electromagnetic coils are formed on the multilayer wiring substrate. With this structure, the electromagnetic coils can be made thin, and flexibility can be improved.

Preferably, magnetic members are provided to center parts of the electromagnetic coils. With this structure, the magnetic members can be synchronously moved, with turn-on/off of the electromagnetic coils, according to magnetic gradient. Namely, the blood flow of the human body can be accelerated by varying concavity and convexity of a surface in a region which is included in a surface of the pressure-sensitive mat system to contact the human body and in which the pressure is made high for a long time.

Advantageous Effects of Invention

By employing the present invention, the cloth is coated with the conductive carbon black, so that the pressure-sensitive sensor, which has flexibility with little uncomfortable feeling for the human body and whose size is not restricted by a size of facility, e.g., plating facility, can have a large size corresponding to that of the human body, can perform wide-range pressure distribution measurement and can stably measure the pressurizing force in the surface-contact state. The conductive carbon black has the branch structure, reduces resistance values by the tunnel effect and can be obtained with at a lower price than noble metals and conductive high polymer compounds, so that high productivity can be enabled with restraining the material cost. A resistance value of the conductive cloth is greater than that of the first-electrode cloth or cloths and the second-electrode cloth or cloths, so that fluctuation of resistance values according to measurement positions and cross talk can be reduced. Further, the areas of intersection are formed so as to have the matrix structure, so that accuracy of measuring the pressurizing force in each of the areas of intersection can be improved.

DESCRIPTION OF EMBODIMENTS

First Embodiment

Figure 1:
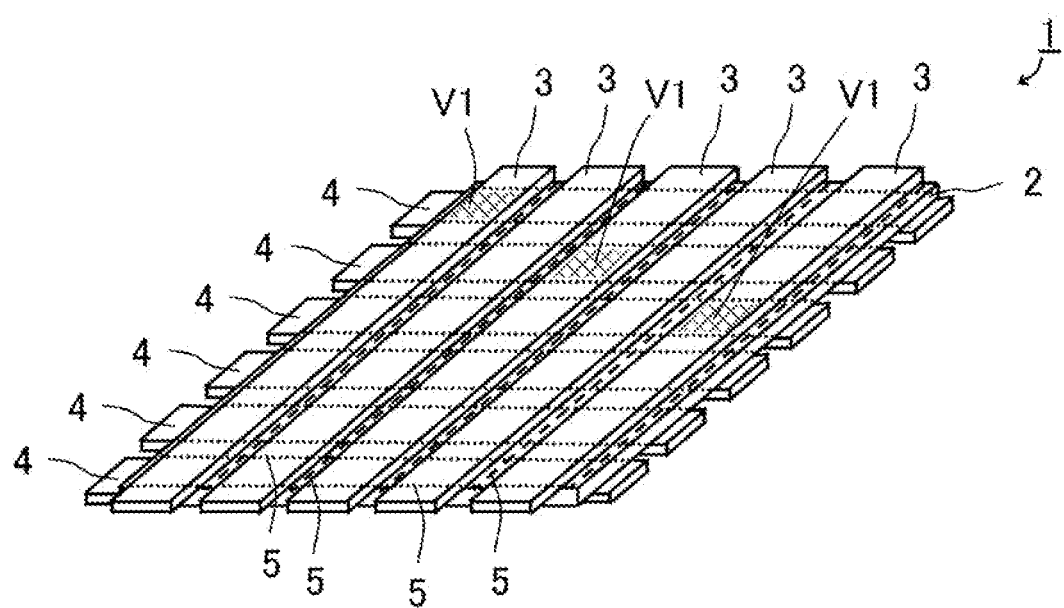
FIG. 1 is a schematic perspective view of an example of a pressure-sensitive sensor relating to a first embodiment of the present invention.
Figure 1:
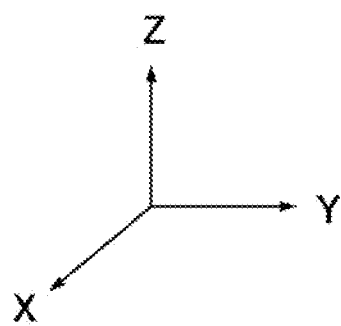
Figure 2:
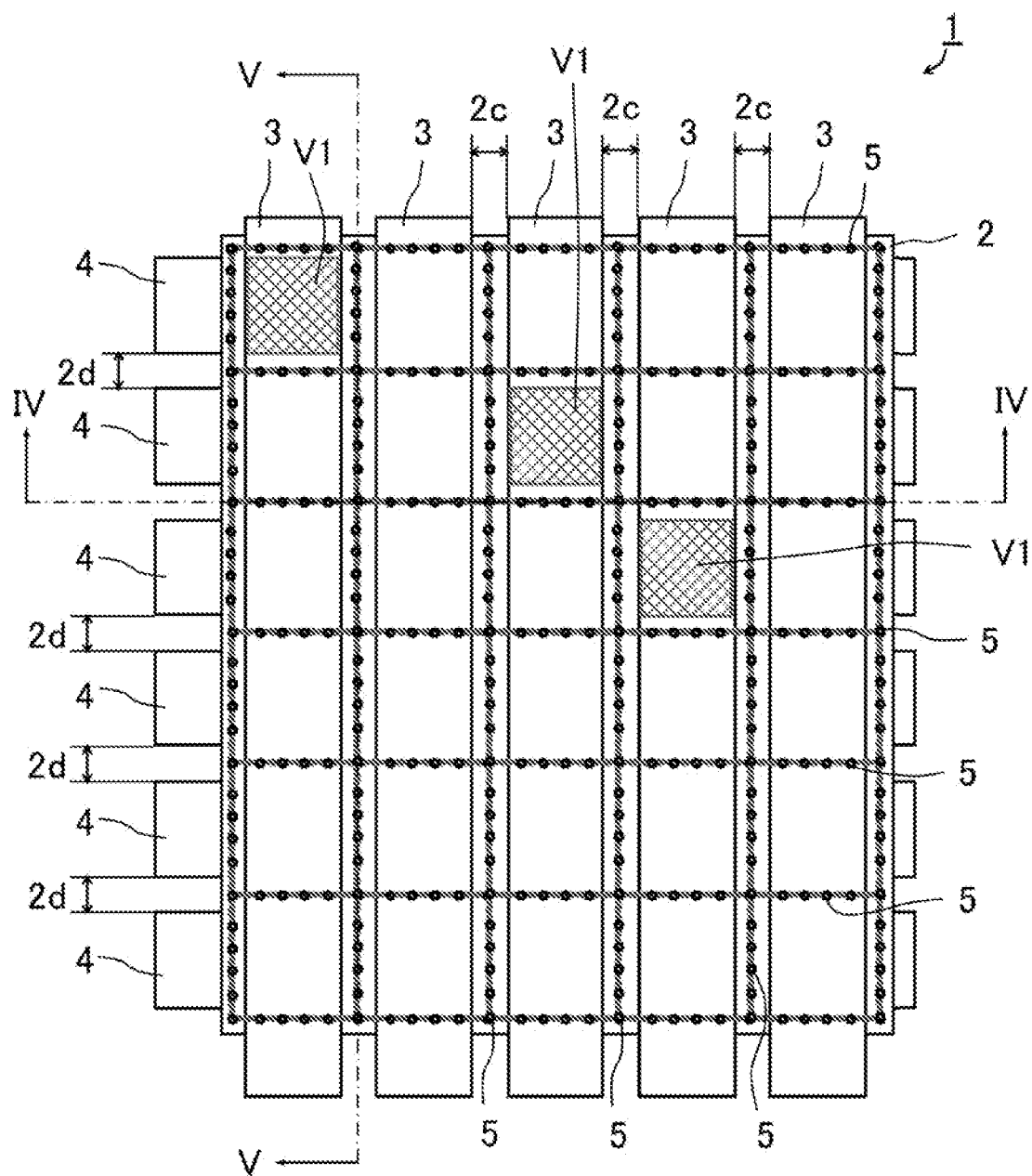
FIG. 2 is a schematic plan view of the pressure-sensitive sensor shown in FIG. 1.
Figure 3A:
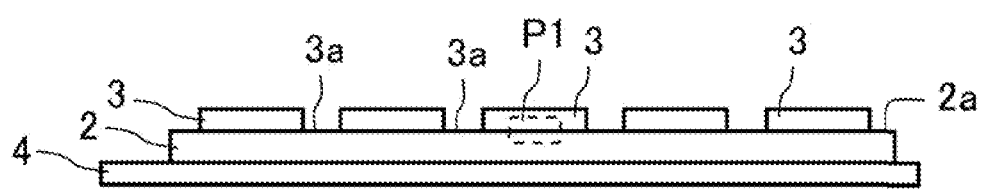
FIG. 3A is a schematic front view of the pressure-sensitive sensor shown in FIG. 1.
Figure 3A:
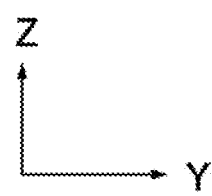
Figure 3B:
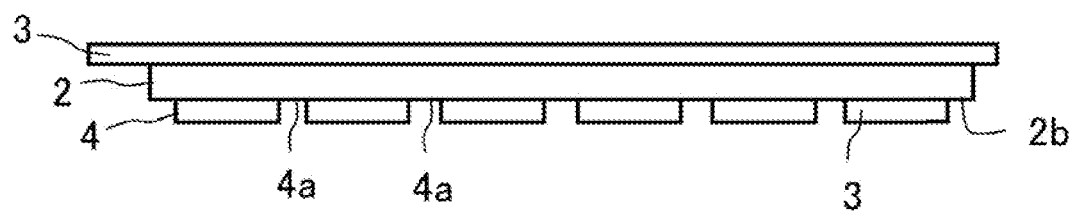
FIG. 3B is a schematic side view of the pressure-sensitive sensor shown in FIG. 1.
Figure 3B:
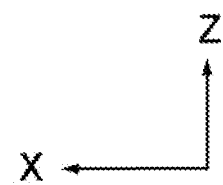

Embodiments of the present invention will now be described in detail with reference to the accompanying drawings. FIG. 1 is a schematic perspective view of an example of a pressure-sensitive sensor 1 relating to a first embodiment of the present invention. FIG. 2 is a schematic plan view of the pressure-sensitive sensor 1 relating to the present embodiment. FIG. 3A is a schematic front view of the example of the pressure-sensitive sensor relating to the present embodiment, and FIG. 3B is a schematic side view of the example of the pressure-sensitive sensor relating to the present embodiment. For convenience of explanation, a cover cloth, signal wires, etc. are omitted in FIG. 1, etc. Note that, in all the drawings explaining embodiments, a same symbol is assigned to members having the same function, and repetition of the same explanation will be omitted in some cases.

To easily explain positional relationships of parts of the pressure-sensitive sensor 1, directions X, Y and Z are shown by arrows in the drawings. When actually using the pressure-sensitive sensor 1, a direction to be directed is not limited to the shown direction, and it may be directed in any directions without any problem. Note that, a first-surface 2a and a second-surface 2b are directed in the opposite directions with respect to each other, a relative positional relationship is shown, and physical directions are not limited. The first-surface 2a may be replaced with, for example, an upper surface or a front surface. Further, the second-surface 2b may be replaced with, for example, a lower surface or a rear surface.

As shown in FIGS. 1, 2, 3A and 3B, the pressure-sensitive sensor 1 comprises: a square conductive cloth 2; a plurality of first-electrode cloths 3, each of which is formed into a belt-like shape, being arranged at a first-interval 2c on the first-surface 2a of the conductive cloth 2; a plurality of second-electrode cloths 4, each of which is formed into a belt-like shape, being arranged at a second-interval 2d on the second-surface 2b of the conductive cloth 2, in a direction intersecting that of the first-electrode cloths 3; and non-conducting sewing threads 5. Here, the first-electrode cloths 3 are arranged, on the first-surface 2a of the conductive cloth 2, in almost parallel, the second-electrode cloths 4 are arranged, on the second-surface 2b of the conductive cloth 2, in almost parallel, and the second-electrode cloths 4 are arranged almost orthogonal to the first-electrode cloths 3. Note that, the shape of the conductive cloth 2, the first-electrode cloths 3 and the second-electrode cloths 4 are not limited to the square shape, and it may be a square shape having rounded corners or an elliptical shape in some cases.

Figure 4:
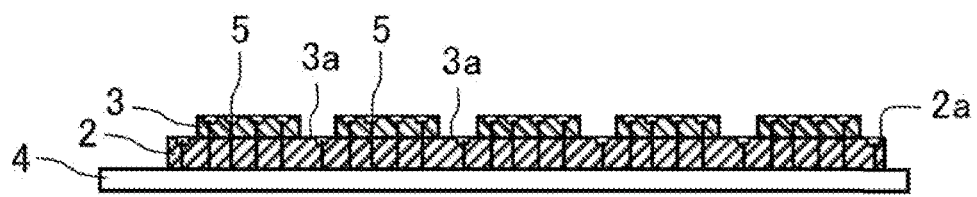
FIG. 4 is a sectional view taken along a line IV-IV shown in FIG. 2.
Figure 4:
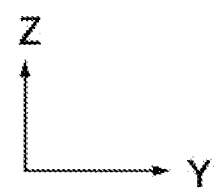
Figure 5:
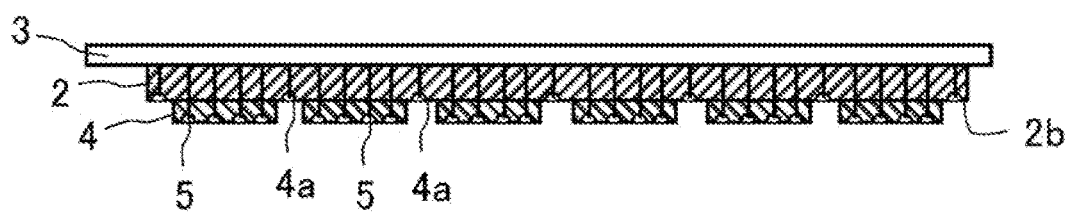
FIG. 5 is a is a sectional view taken along a line V-V shown in FIG. 2.
Figure 5:
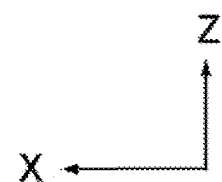

Here, as shown in FIG. 4, in the pressure-sensitive sensor 1, each of the second-electrode cloths 4 is sewn to the conductive cloth 2, in a first-clearance 3a between the adjacent first-electrode cloths 3 and 3, with the sewing threads 5. And, as shown in FIG. 5, each of the first-electrode cloths 3 is sewn to the conductive cloth 2, in a second-clearance 4a between the adjacent second-electrodes 4 and 4, with the sewing threads 5. Further, areas V1 of intersection, which are formed by the first-electrode cloths 3 and second-electrode cloths 4, are formed so as to have a matrix structure in plan view. In FIGS. 1 and 2, the areas V1 of intersection are exemplified as hatched square areas.

In the example shown in FIG. 2, the sewing threads 5 are sewn to enclose the areas V1 of intersection. Further, the sewing threads 5 are sewn at outside positions of the four corners of each of the areas V1 of intersection. With this structure, a leak current from the one area V1 of intersection to other areas V1 thereof can be reduced by sewing the sewing threads 5, so that S/N ratio of detection signals, which are outputted in response to a pressurizing force, can be improved.

Further, as shown in FIG. 4, parts of the first-electrode cloths 3 to which the sewing threads 5 are sewn are concaved by tension of the sewing threads 5. And, as shown in FIG. 5, parts of the second-electrode cloths 4 to which the sewing threads 5 are sewn are concaved by tension of the sewing threads 5. With this structure, non-sensitive parts are formed, at the sewn parts, by stranglehold in the vertical direction caused by sewing the sewing threads 5, and fluctuations of resistance values at positions, at which no areas V1 of intersection are formed, is regulated by forming the non-sensitive parts, so that S/N ratio of detection signals, which are outputted in response to the pressurizing force, can be improved. In some cases, the sewing threads are sewn at positions of the four corners of each of the areas V1 of intersection, and the effects equivalent to those of the example shown in FIG. 4 can be obtained as well.

Figure 6A:
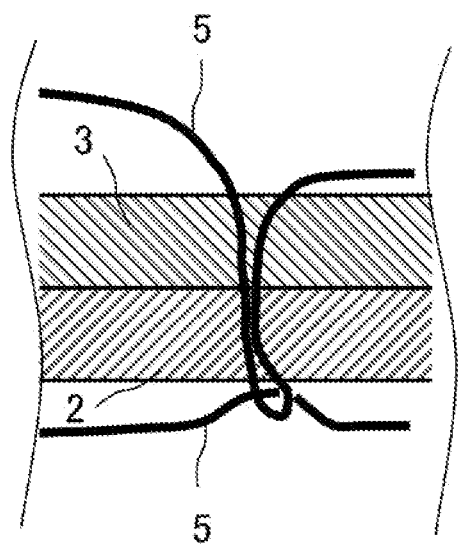
FIG. 6A is a schematic sectional view, in which a knot is formed by passing a lower sewing thread through a loop-shaped upper sewing thread which has been penetrated through an electrode cloth and a conductive cloth by a sewing machine.
Figure 6B:
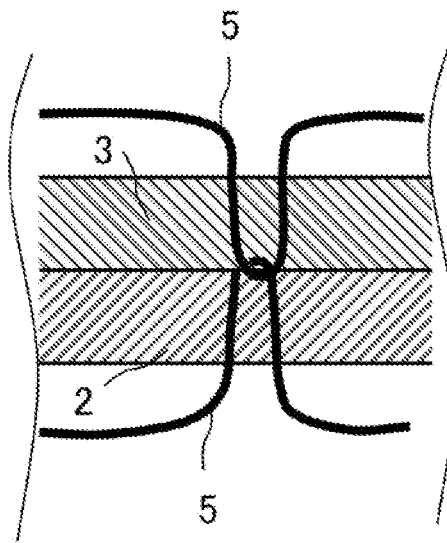
FIG. 6B is a schematic sectional view, in which the knot is located between the electrode cloth and the conductive cloth by pulling the knot upward.
Figure 6C:
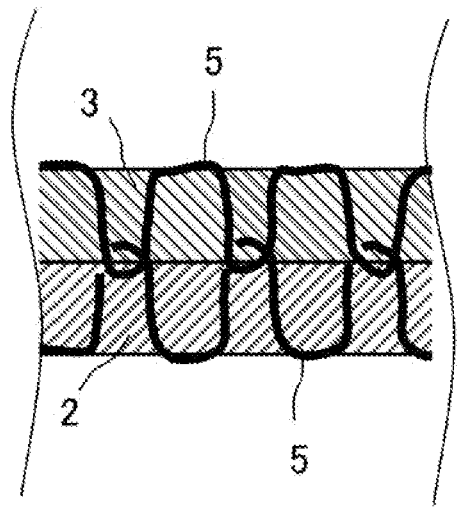
FIG. 6C is a sectional view, in which the electrode cloth and the conductive cloth are sewn to each other, by repeating the operation of forming the knots, with moving the both cloths in a prescribed direction.

FIGS. 6A, 6B and 6C are schematic sectional views exemplifying the steps of sewing the first-electrode cloth 3 and the conductive cloth 2 by a sewing machine. As an example, in case of performing lock stitching, the lower sewing threads 5 are passed through loop-shaped upper sewing threads 5, which are penetrated through the first-electrode cloth 3 and the conductive cloth 2, by the sewing machine, so that knots are formed (see FIG. 6A); then, the knots are located between the first-electrode cloth 3 and the conductive cloth 2 by pulling the knots upward (see FIG. 6B); and the first-electrode cloth 3 and the conductive cloth 2 are sewn to each other, by repeating the operation of forming the knots, with moving the both cloths in a prescribed direction (see FIG. 6C). In case of sewing the second-electrode cloth 4 and the conductive cloth 2 by the sewing machine too, the sewing steps are equivalent to those shown in FIGS. 6A, 6B and 6C.

In the present embodiment, a width of the first-electrode cloths 3 in a transverse direction is wider than that of the first-intervals 2c in a transverse direction, and a width of the second-electrode cloths 4 in a transverse direction is wider than that of the second-intervals 2d in a transverse direction. With this structure, a leak current from an adjacent measurement position can be reduced, so that S/N ratio of detection signals, which are outputted in response to the pressurizing force, can be improved. For example, the width of the first-electrode cloths 3 and the second-electrode cloths 4 in the transverse direction are 10-100 [mm]. And, for example, the width of the first-intervals 2c and the second-intervals 2d in the transverse direction are 1-10 [mm].

In the present embodiment, a thickness of the conductive cloth 2 is smaller than the width of the first-intervals 2c in the transverse direction, and the thickness of the conductive cloth 2 is smaller than the width of the second-intervals 2d in the transverse direction. With this structure, a leak current from an adjacent measurement position can be reduced, so that S/N ratio of detection signals, which are outputted in response to the pressurizing force, can be improved. For example, the thickness of the conductive cloth 2 is 0.3-0.6 [mm]. And, for example, the thicknesses of the first-electrode cloths 3 and the second-electrode cloths 4 are 0.2-0.6 [mm].

In some cases, electrodes of the first-electrode cloths 3 are formed only on surfaces facing the first-surface 2a of the conductive cloth 2, so that a cost of an electrode material and a production cost can be reduced. On the other hand, in some cases, electrodes of the first-electrode cloths 3 are formed on upper surfaces and lower surfaces of the first-electrode cloths 3, or electrodes are formed throughout whole circumferences of the first-electrode cloths 3. In these cases, any of the upper surfaces and the lower surfaces of the first-electrode cloths 3 may be stacked onto the conductive cloth 2, so that it is easy to produce. Further, in some cases, electrodes of the first-electrode cloths 3 are made conductive in a thickness direction of the first-electrode cloths 3, so that reliability of conductivity of the electrodes can be improved.

In some cases, electrodes of the second-electrode cloths 4 are formed only in surfaces facing the second-surface 2b of the conductive cloth 2, so a cost of an electrode material and the production cost can be reduced. On the other hand, in some cases, electrodes of the second-electrode cloths 4 are formed in upper surfaces and lower surfaces of the second-electrode cloths 4, or electrodes are formed throughout whole circumferences of the second-electrode cloths 4. In these cases, any of the upper surfaces and the lower surfaces of the second-electrode cloths 4 may be stacked onto the conductive cloth 2, so that it is easy to produce. Further, in some cases, electrodes of the second-electrode cloths 4 are made conductive in a thickness direction of the second-electrode cloths 4, so that reliability of conductivity of the electrodes can be improved.

Figure 7A:
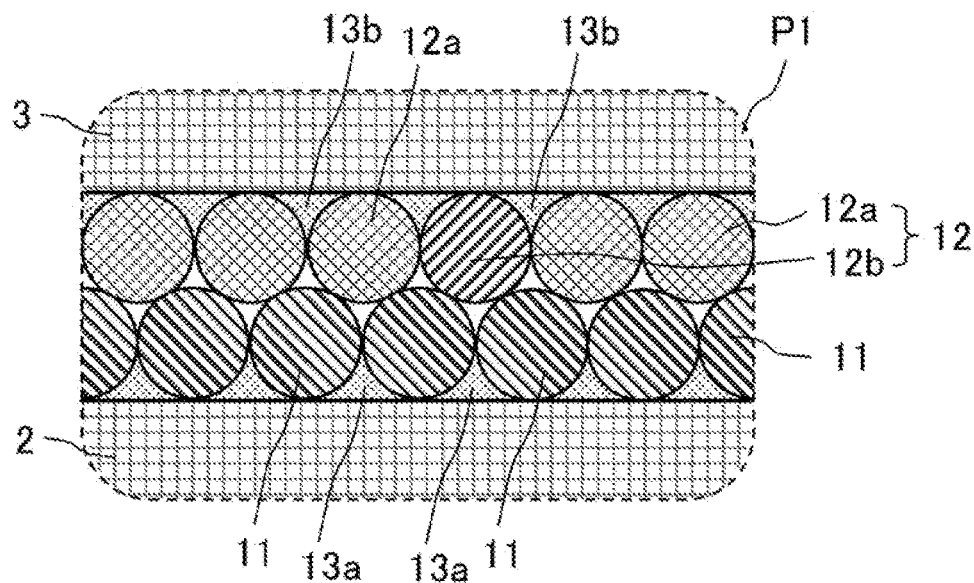
FIG. 7A is a schematic sectional view schematically showing an example of a contact state between a first-electrode cloth and the conductive cloth.
Figure 7B:
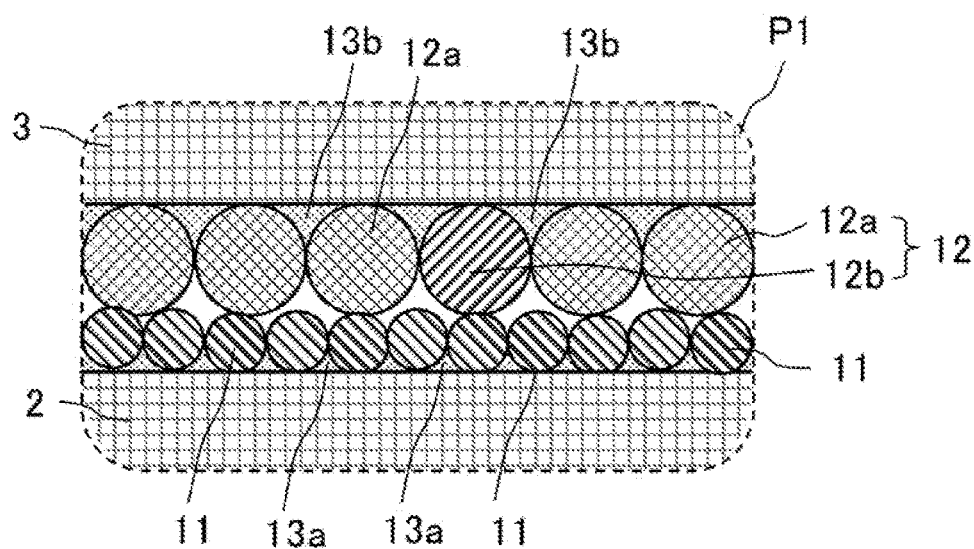
FIG. 7B is a schematic sectional view schematically showing another example of a contact state between the first-electrode cloth and the conductive cloth.
Figure 7C:
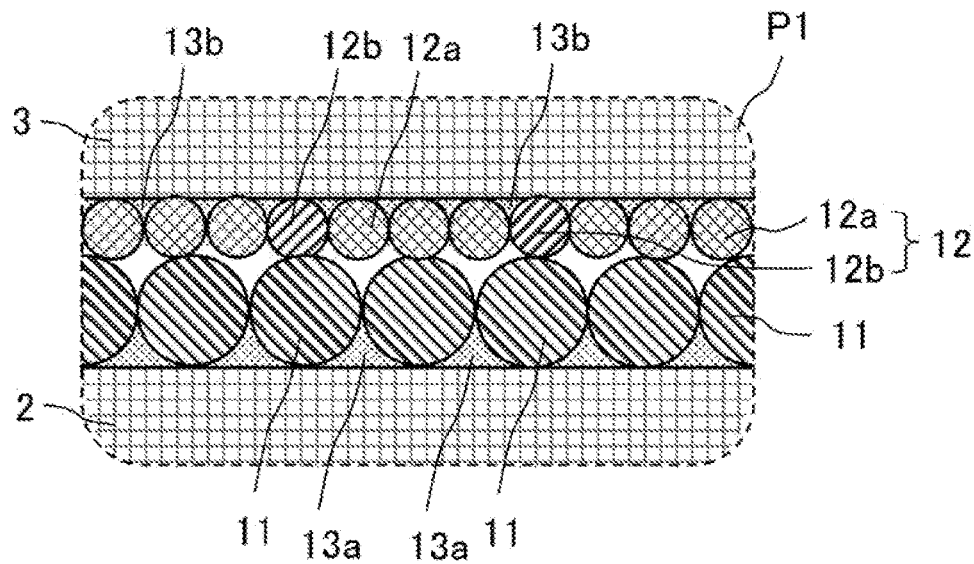
FIG. 7C is a schematic sectional view schematically showing a further example of a contact state between the first-electrode cloth and the conductive cloth.

FIGS. 7A, 7B and 7C are enlarged views of a part P1 which is enclosed by a dotted line in FIG. 3A, and they are schematic sectional views showing a state where the first-electrode cloth 3 and the conductive cloth 2 contact each other. Here, first-conductive particles 11 are composed of conductive carbon black, and second-conductive particles 12 are composed of conductive metal particles 12a and conductive carbon black 12b. The conductive carbon black 11 is adhered to the conductive cloth 2 by binder resin 13a, and the conductive metal particles 12a and the conductive carbon black 12b are adhered to the first-electrode cloth 3 by binder resin 13b. A contact state of the second-electrode cloth 4 and the conductive cloth 2 is equivalent to that shown in FIGS. 7A, 7B and 7C. Namely, the second-conductive particles 12 having greater electrical conductivity than the first-conductive particles 11 are applied to coat the first-electrode cloths 3 and the second-electrode cloths 4.

In the present embodiment, the conductive cloth 2 is electrically conductive in the thickness direction, the longitudinal direction and the transverse direction by a structure of the first-conductive particles 11 (not shown). Further, the first-electrode cloths 3 are electrically conductive in the thickness direction, the longitudinal direction and the transverse direction by structures of the second-conductive particles 12a and the conductive carbon black 12b (not shown). The second-electrode cloths 4 are equivalent to the first-electrode cloths 3.

In the present embodiment, the conductive carbon black, whose average particle diameter of the primary particles is 100 nm or less, is composed of one or more out of ketjenblack, acetyleneblack, channelblack and furnaceblack. With this structure, a required resistance value can be obtained by adding a small quantity thereof, so that the conductive cloth having superior abrasion resistance and superior flexibility can be provided.

Furnaceblack is produced by a furnace method, in which conductive carbon black is obtained by performing incomplete combustion of oil or gas. Furnaceblack can be easily mass-produced, and its particle diameter and structure can be easily controlled.

Channelblack is produced by a channel method, in which a natural gas is combusted, and matters separated on channel steel are collected. Channelblack has many surface functional groups, so it is suitable for coating.

Acetyleneblack is produced by an acetylene method, in which an acetylene gas is thermally decomposed. Acetyleneblack has high electrical conductivity and includes a small quantity of impure substances.

Ketjenblack is produced by an oil furnace method, in which conductive carbon black is produced by, roughly speaking, performing incomplete combustion of oil including a small quantity of impure substances, separating a by-product gas, and granulating and drying a precursor. Unlike other conductive carbon blacks, ketjenblack has a hollow shell-like structure, so its electrical conductivity is higher than that of acetyleneblack.

As an example, a catalogue value of a BET-specific surface area of ketjenblack EC300J, which is produced by Lion Specialty Chemicals Co., Ltd., is 800 [$m^2/g$], and a catalogue value of a BET-specific surface area of ketjenblack EC600JD is 1270 [$m^2/g$] or more, so they are 10 times or more greater than a BET-specific surface area of standard acetyleneblack. Therefore, high electrical conductivity can be obtained by adding a small quantity thereof, so that the conductive cloth having superior abrasion resistance and superior flexibility can be provided.

As shown in FIG. 7A, an outer diameter of the first-conductive particles 11 and that of the second-conductive particles 12 are almost same, and this state is the best mode in which contact resistance between the first-electrode cloths 3 and the conductive cloth 2 is minimized. In the example shown in FIG. 7A, a contact area between the first-electrode cloths 3 and the conductive cloth 2 is maximized, a required contact area is sufficiently secured, and resistance values of the first-electrode cloths 3 are suitably smaller than that of the conductive cloth 2, so that fluctuation of resistance values according to measurement positions and cross talk can be reduced. The second-electrode cloths 4 are equivalent to the first-electrode cloths 3.

As shown in FIG. 7B, an outer diameter of the first-conductive particles 11 is 0.5 time or more as large as that of the second-conductive particles 12 and 2.0 times or less as large as the same, and this state is a better mode in which contact resistance between the first-electrode cloths 3 and the conductive cloth 2 is suitably small. In the example shown in FIG. 7B, most of the second-conductive particles 12 of the first-electrode cloths 3 contact most of the first-conductive particles 11 of the conductive cloth 2, and a required contact area is secured, so that fluctuation of resistance values according to measurement positions and cross talk can be reduced. The second-electrode cloths 4 are equivalent to the first-electrode cloths 3.

As shown in FIG. 7C, an outer diameter of the first-conductive particles 11 is 2.0 times or less as large as that of the second-conductive particles 12 and 0.5 time or more as large as the same, and this state is a better mode in which contact resistance between the first-electrode cloths 3 and the conductive cloth 2 is suitably small. In the example shown in FIG. 7C, most of the second-conductive particles 12 of the first-electrode cloths 3 contact most of the first-conductive particles 11 of the conductive cloth 2, and the required contact area is secured, so that fluctuation of resistance values according to measurement positions and cross talk can be reduced. The second-electrode cloths 4 are equivalent to the first-electrode cloths 3.

As shown in FIGS. 7A, 7B and 7C, in the present embodiment, assuming that the average particle diameter of the primary particles of the first-conductive particles 11 is a standard, the average particle diameter of the primary particles of the second-conductive particles 12 is within a range between 0.5 time or more as large as the standard and 2.0 times or less as large as the same. With this structure, the contact area between the first-electrode cloths 3 and the conductive cloth 2 and that between the second-electrode cloths 4 and the conductive cloth 2 can be increased, so that the contact states can be stabilized.

In the present embodiment, assuming that a weight of the conductive cloth 2 is a standard, a weight of the first-conductive particles 11 is 5% or less of the standard. With this structure, the conductive cloth 2 having superior abrasion resistance and superior flexibility can be provided, and a material cost can be reduced.

In the present embodiment, a mixture of the first-conductive particles 11 and the binder resin 13a whose rupture elongation is 100% or more is applied to coat the conductive cloth 2. And a mixture of the second-conductive particles 12 and the binder resin 13b whose rupture elongation is 100% or more is applied to coat the first-electrode cloths 3. Further, a mixture of the second-conductive particles 12 and the binder resin 13b whose rupture elongation is 100% or more is applied to coat the second-electrode cloths 4. With this structure, the pressurizing force can be stably measured with utilizing the flexibility of the conductive cloth 2, the first-electrode cloths 3 and the second-electrode cloths 4.

In the present embodiment, all of the conductive cloth 2, the first-electrode cloths 3 and the second-electrode cloths 4 are composed of woven fabric, or all of the conductive cloth 2, the first-electrode cloths 3 and the second-electrode cloths 4 are composed of knitted fabric. With this structure, the pressure-sensitive sensor 1 has superior stretch ability, and the pressure-sensitive sensor 1, which has flexibility with little uncomfortable feeling for a human body, has a large size corresponding to the human body and is capable of performing wide-range pressure distribution measurement, can be provided.

The first-conductive particles 11 are adhered to a surface of a base cloth of the conductive cloth 2 and in fibers thereof by the binder resin 13a. And the second-conductive particles 12 are adhered to surfaces of base cloths of the first-electrode cloths 3 and in fibers thereof by the binder resin 13b. Further, the second-conductive particles 12 are adhered to surfaces of base cloths of the second-electrode cloths 4 and in fibers thereof by the binder resin 13b.

As an example, in the conductive cloth 2, the conductive carbon black (the first-conductive particles 11) and the binder resin 13a are applied to coat the base cloth composed of fibers. As an example, in the first-electrode cloths 3 and the second-electrode cloths 4, the conductive metal particles (the second-conductive particles 12) and the binder resin 13b are applied to coat the base cloths composed of fibers. As an example, the first-electrode cloths 3 and the second-electrode cloths 4 are composed of the same material.

In the present embodiment, the conductive metal particles are applied to coat the first-electrode cloths 3 and the second-electrode cloths 4, and the conductive carbon black is applied to coat the conductive cloth 2, so that surface resistivities of both of the first-electrode cloths 3 and the second-electrode cloths 4 are more than two orders of value smaller than that of the conductive cloth 2. With this structure, influences of the resistances of the first-electrode cloths 3 and the second-electrode cloths 4 in the longitudinal direction are reduced, so that S/N ratio of detection signals, which are outputted in response to the pressurizing force, can be improved. Namely, influences of measured resistances in the areas V1 of intersection, which act as pressure-sensitive parts, can be almost ignored. And the conductive cloth 2 having superior decentralized stabilization can be produced with the conductive carbon black, which is more inexpensive than conductive metal particles. Further, fluctuation of resistance values according to measurement positions can be reduced, and cross talk between the areas V1 and V1 of intersection can be reduced.

For example, the base cloths may be composed of synthetic fibers, e.g., nylon, polyester, rayon, acrylic, polyamide, or natural fibers, e.g., cotton, linen. In a medical field, an autoclave sterilization treatment will be performed, so the above described fibers, which have high resistance properties to the autoclave sterilization treatment, are suitable ones.

As an example, the base cloths may be composed of woven fabric, knitted fabric or nonwoven fabric. A thickness of threads or fibers constituting the base cloths is, for example, 50-200 denier. In case that the base cloths are composed of knitted fabric or nonwoven fabric, a contact area with respect to the human body can be increased, and a contact resistance can be reduced. In case that the base cloths are composed of knitted fabric, the knitted fabric has more superior stretch ability than the woven fabric and the nonwoven fabric, so that the superior base cloths can be provided.

As an example, the first-conductive particles 11 are composed of conductive carbon black, e.g., ketjenblack. The conductive carbon black has a branch structure, can reduce a resistance value by tunnel effect and can be obtained with at a lower price than noble metals and conductive high polymer compounds. Especially, in case of using ketjenblack, the required resistance value can be obtained by adding a small quantity thereof, so that the conductive cloth having superior abrasion resistance and superior flexibility can be provided.

As an example, the second-conductive particles 12 are composed of conductive metal powders, conductive metal fibers, conductive high polymers, conductive carbon black, or mixture thereof. The conductive metals may be, for example, gold (Au), silver (Ag), copper (Cu), nickel (Ni), aluminum (Al) and other known conductive metals. The conductive high polymers may be, for example, poly(3,4-ethylene dioxythiophene) (PEDOT), poly(3,4-ethylene dioxythiophene) doped with poly(4-styrenesulfonic acid) (PEDOT/PSS), tetracyanoquinodimethane (TCNQ), polypyrrole (PPy), polyaniline (PANI), polythiophene (PT) and other known high polymers.

As an example, the binder resin 13*a* and the binder resin 13*b* are composed of thermoplastic resin, thermosetting resin or photosetting resin. For example, the binder resin 13*a* and the binder resin 13*b* may be composed of polyamide (PA), polycarbonate (PC), polyethylene terephthalate (PET), polyurethane (PU), polyester (PEs) or other known synthetic resin.

Coating may be performed by an immersion coating method, a spray coating method, a roll coating method, a bar coating method, an electrocoating method, other known coating methods or combinations thereof.

The sewing threads 5 are composed of synthetic fibers, e.g., nylon, polyester, rayon, acrylic, polyamide, or natural fibers, e.g., cotton, linen. A thickness of the sewing threads 5 is, for example, 20-200 denier.

For example, the sewing operation is manually performed or performed by a sewing machine. Lock stitching, chain stitching, whip stitching, flat stitching or other known stitching manners may be employed for the sewing operation. In case of the lock stitching, the parts to which the sewing threads 5 are sewn become non-stretchable seams in the first-surface 2*a* (the front surface) and the second-surface 2*b* (the rear surface), non-sensitive parts are formed, and fluctuations of resistance values at positions, at which no areas V1 of intersection are formed, can be regulated, so that the areas V1 of intersection, which are formed so as to have the matrix structure, can easily act as independent pressure cells capable of respectively outputting electric signals.

Figure 8:
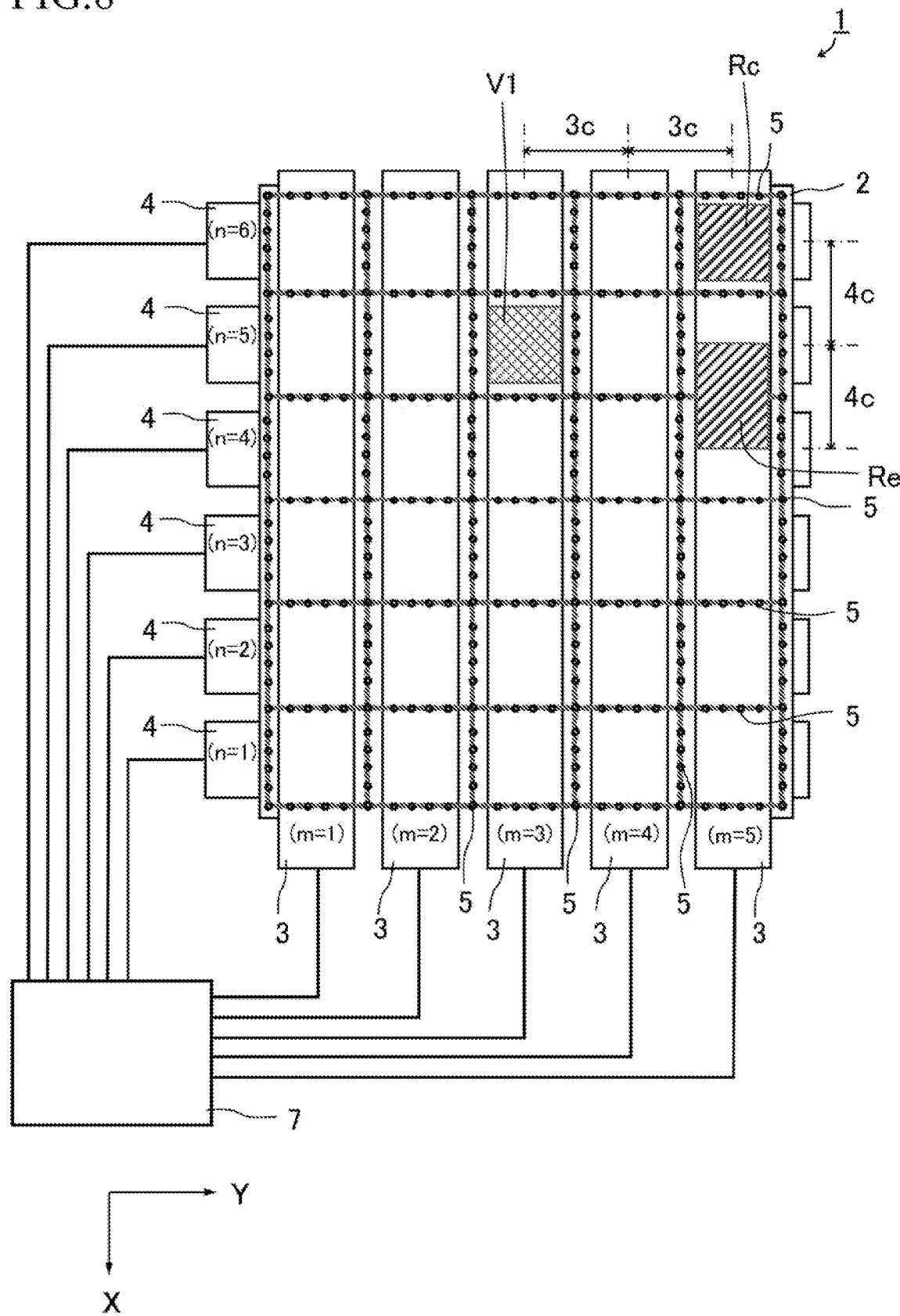
FIG. 8 is a schematic plan view of the example of the pressure-sensitive sensor relating to the first embodiment, in which a controller is connected.

FIG. 8 is a schematic plan view of an example of the pressure-sensitive sensor 1 relating to the first embodiment, in which a controller 7 is connected. The controller 7 has a CPU for controlling a signal wire switching circuit, a signal detector, an A/D converter, semiconductor memories and an arithmetic circuit.

In the pressure-sensitive sensor 1, signal wires are connected to longitudinal end parts of the first-electrode cloths 3 and the second-electrode cloths 4, scan is performed at a frequency of, for example, 10-100 [Hz] by the switching circuit included in the controller 7, resistance values of the areas V1 of intersection, which are formed so as to have the matrix structure, are respectively detected, with millisecond order, by the signal detector, the detected signals are A/D-converted by the A/D converter, data are stored in the semiconductor memories and calculated by the arithmetic circuit, and results of calculation are finally displayed on an external display unit as pressure values, pressure distribution or pressure values plus pressure distribution. For example, a personal computer including an interface substrate for signal-connecting to the pressure-sensitive sensor 1 may be used as the controller 7 and the external display unit.

In the present embodiment, the [m] number of first-electrode cloths 3 are provided at the first-interval 2*c* on the first-surface 2*a* of the conductive cloth 2, the [n] number of second-electrode cloths 4 are provided at the second-interval 2*d* on the second-surface 2*b* of the conductive cloth 2, in the direction intersecting that of the first-electrode cloths 3, and the areas V1 of intersection, which are the intersection areas between the first-electrode cloths 3 and the second-electrode cloths 4, are formed so as to have the matrix structure. Here, the numbers [m] and [n] are natural numbers 2 or more, and the numbers are, for example, m=5 and n=6 in the example shown in FIG. 8.

In the present embodiment, a resistance value Re [Ω], which is an average resistance value of the two areas V1 and V1 of intersection longitudinally adjacent to each other in the longitudinal direction, with respect to a resistance value Rc [Ω], which is an average resistance value of the areas V1 of intersection, in the thickness direction, in a state where an external force of 50 [mmHg] is applied, in the compaction direction, to move the first-electrode cloths 3 and the second-electrode cloths 4 close to each other, satisfies the above described Formula (1).

As shown in FIG. 8, in case that an electrode pitch 3*c* of the first-electrode cloths 3 in a row direction is equal to an electrode pitch 4*c* of the second-electrode cloths 4 in a column direction, the above described Formula (1) is satisfied.

On the other hand, in case that the electrode pitch 3c of the first-electrode cloths 3 and the electrode pitch 4c of the second-electrode cloths 4 are different from each other, the resistance value Re [Ω] is obtained from a weighted average value of an electrode resistance value R1 [Ω] of the first-electrode cloths 3 arranged in the row direction with the electrode pitch 3c and an electrode resistance value R2 [Ω] of the second-electrode cloths 4 arranged in the column direction with the electrode pitch 4c, and it is calculated by the following Formula (2).

Formula (2)

$$Re=(m \times R1 + n \times R2)/(m+n) \qquad (2)$$

FIGS. 15A, 15B, 16A and 16B are resistance-characteristic graphs showing relationships between pressure and resistance.

Figure 15A:
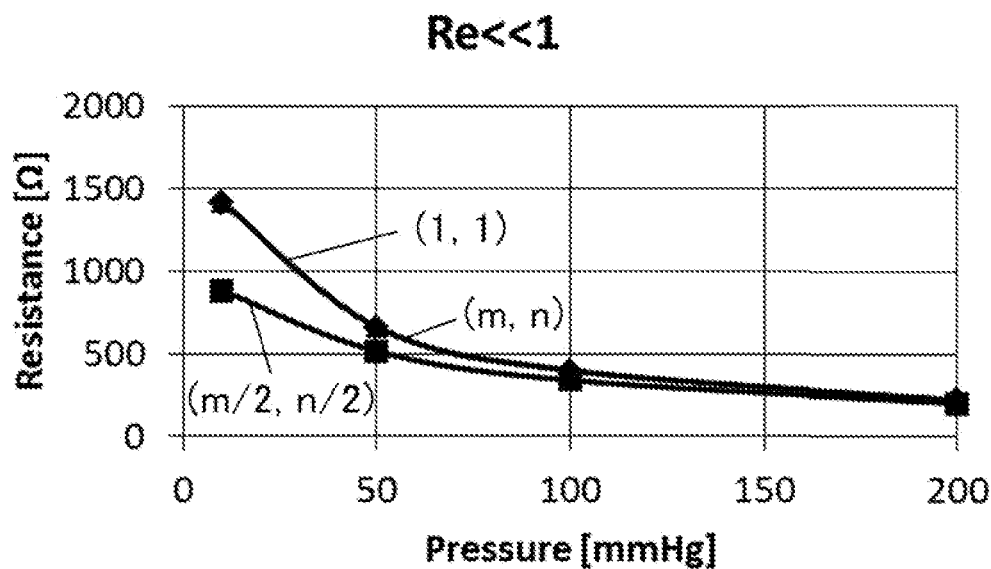
FIG. 15A is a resistance-characteristic graph showing a relationship between pressure and resistance in an area of intersection of the pressure-sensitive sensor.

For example, in case that the first-conductive particles are composed of fine noble metal particles, the resistance value Re [Ω] is much smaller than 1 [Ω] (Re [Ω]<<1 [Ω]). In this case, as shown in FIG. 15A, a resistance-characteristic graph (1, 1) in the areas of intersection forming the matrix arrangement of (m, n) corresponds to a resistance-characteristic graph (m, n) therein. However, the conductive noble metal particles must be applied to plate a cloth, so the material cost must be highly increased, and it is difficult to produce a large size pressure-sensitive sheet.

Figure 15B:
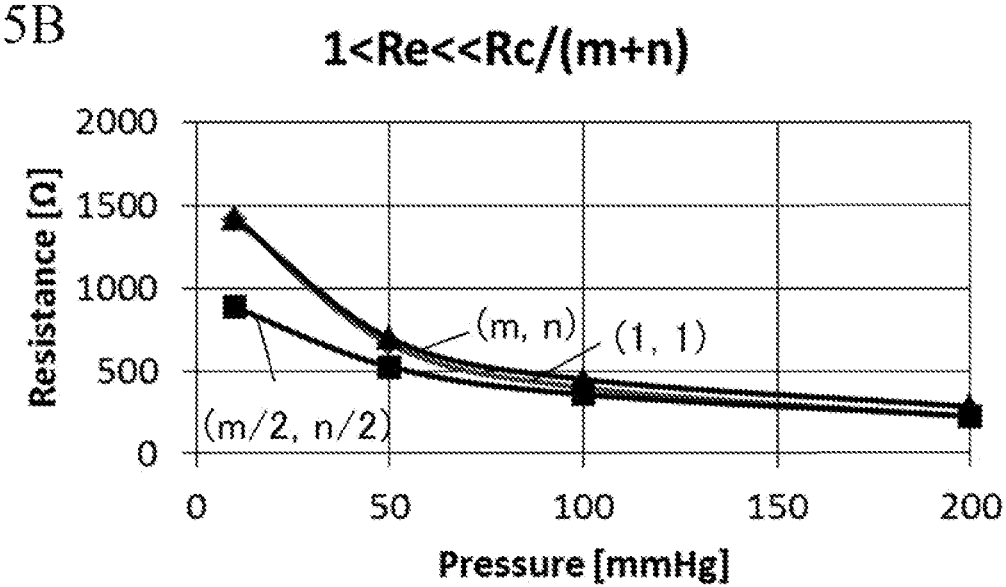
FIG. 15B is a resistance-characteristic graph showing a relationship between pressure and resistance in an area of intersection of the pressure-sensitive sensor.

As an example relating to the present embodiment, the first-conductive particles 11 are composed of the conductive carbon black, the resistance value Re [Ω] is greater than 1 [Ω] (1 [Ω]<Re [Ω]), the second-conductive particles 12 are composed of a mixture of the conductive metal particles 12a and the conductive carbon black 12b, and the resistance value Re [Ω] is much smaller than a value obtained by dividing the resistance value Rc [Ω] by (m+n), i.e., Re [Ω]<<(Rc [Ω]/(m+n). In this case, as shown in FIG. 15B, a resistance-characteristic graph (1, 1) in the areas of intersection forming the matrix arrangement of (m, n) almost corresponds to a resistance-characteristic graph (m, n) therein as well as the example shown in FIG. 15A. When the pressurizing force is about 50 [mmHg], or 50 [mmHg] or more, resistance-characteristic graphs almost correspond to each other in any of the areas of intersection, which are matrically arranged.

With the above described structure, the pressurizing force can be stably measured with utilizing flexibility of the cloths, the size capable of performing wide-range pressure distribution measurement can be enabled, the material cost can be reduced, and productivity can be improved. Further, surface resistances of the belt-like electrodes (the first-electrode cloths 3 and the second-electrode cloths 4), which are provided on the upper side and the lower side of the conductive cloth 2, are more than two orders of value smaller than the surface resistance of the conductive cloth 2, so that accuracy of measuring the pressurizing force in each of the areas V1 of intersection can be improved.

Figure 16A:
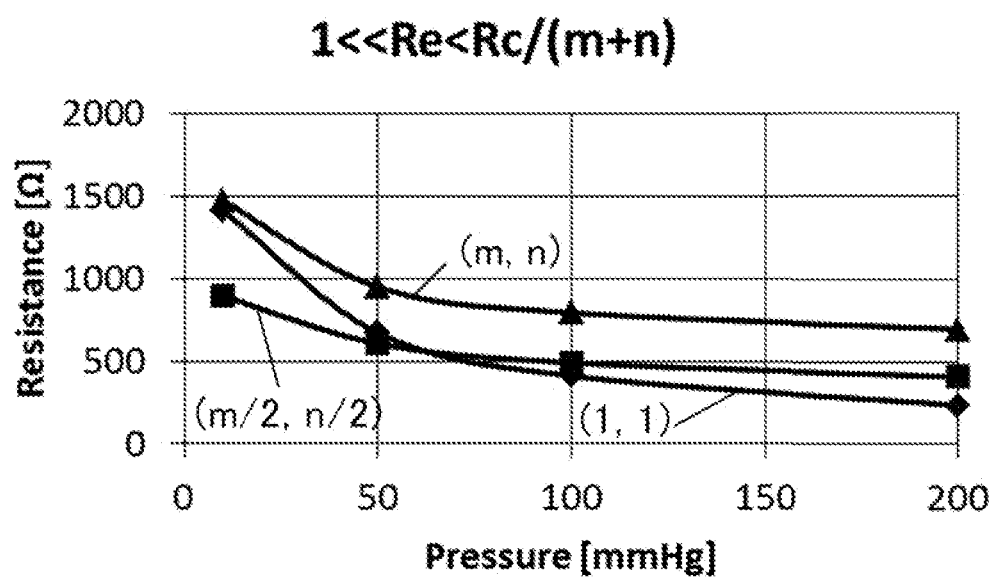
FIG. 16A is a resistance-characteristic graph showing a relationship between pressure and resistance in an area of intersection of the pressure-sensitive sensor.

As an example relating to the present embodiment, the first-conductive particles 11 are composed of the conductive carbon black, the resistance value Re [Ω] is much greater than 1 [Ω] (1 [Ω]<<Re [Ω]), the second-conductive particles 12 are composed of a mixture of the conductive metal particles 12a and the conductive carbon black 12b, and the resistance value Re [Ω] is smaller than a value obtained by dividing the resistance value Rc [Ω] by (m+n), i.e., Re [Ω]<Rc [Ω]/(m+n). In this case, as shown in FIG. 16A, in comparison with the graphs shown in FIGS. 15A and 15B, resistance values of a resistance-characteristic graph (1, 1) in the areas of intersection forming the matrix arrangement of (m, n) and those of a resistance-characteristic graph (m, n) therein are dispersed. In this case, the dispersion of the resistance values is suppressed to two times or less, so that the pressure-sensitive sensor can be used, with no difficulty, by performing calibration in each of the areas of intersection.

Figure 16B:
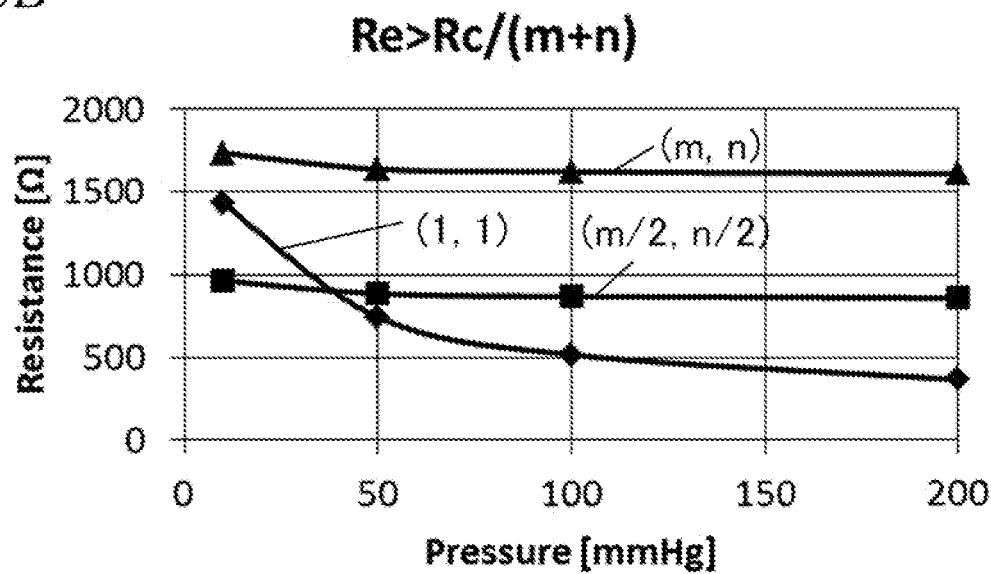
FIG. 16B is a resistance-characteristic graph showing a relationship between pressure and resistance in an area of intersection of the pressure-sensitive sensor.

For example, the resistance value Re[Ω] is greater than a value obtained by dividing the resistance value Rc [Ω] by (m+n), i.e., Re [Ω]>Rc [Ω]/(m+n). In this case, as shown in FIG. 16B, in comparison with the graphs shown in FIGS. 15B and 16A, resistance values of a resistance-characteristic graph (1, 1) in the areas of intersection forming the matrix arrangement of (m, n) and those of a resistance-characteristic graph (m, n) therein are much dispersed. In this case, the dispersion of the resistance values exceeds two times, so it is difficult to use as the pressure-sensitive sensor even if calibration is performed in each of the areas of intersection.

Successively, another example of the pressure-sensitive sensor 1 relating to the first embodiment will be explained below.

Figure 9:
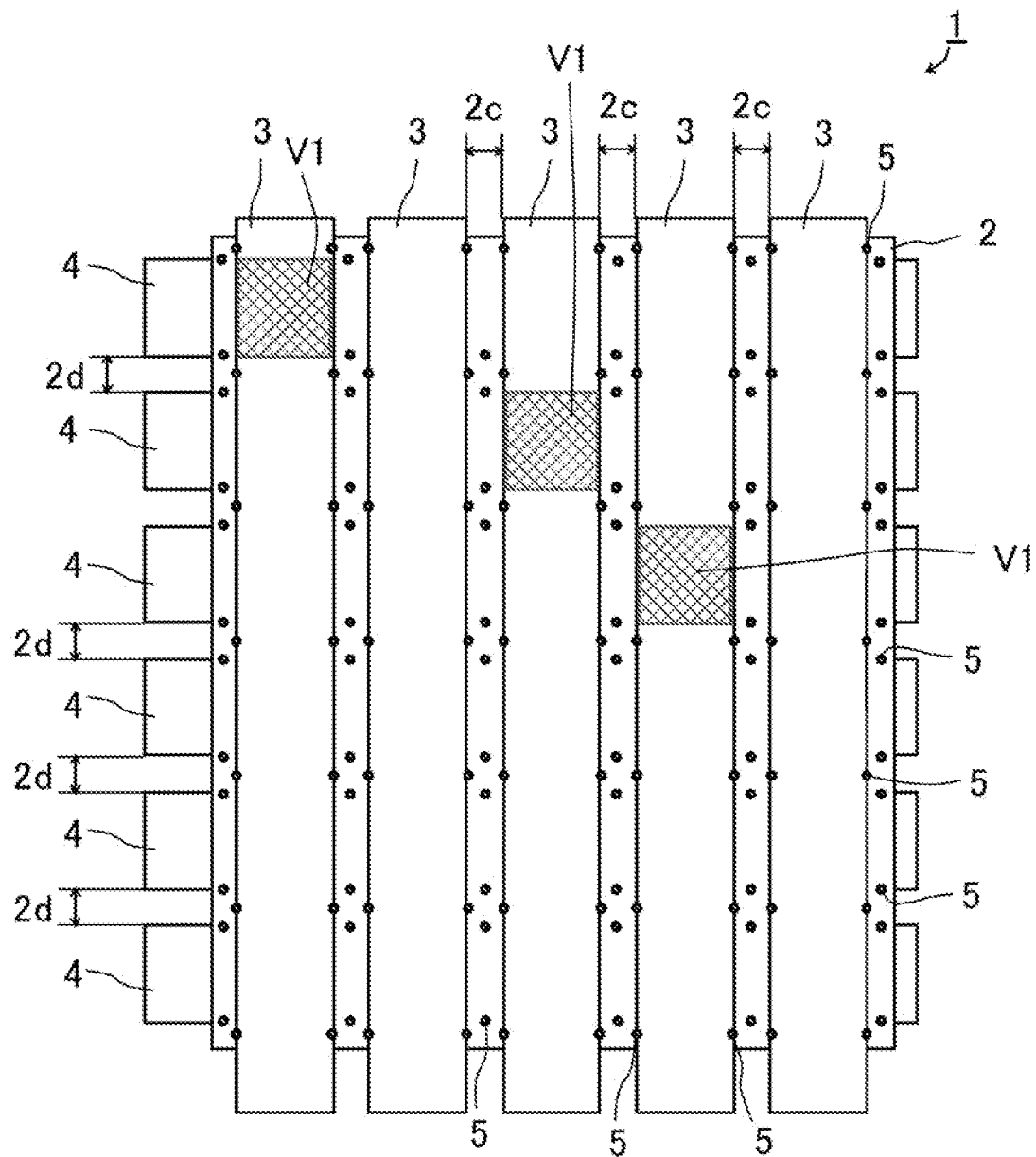
FIG. 9 is a schematic plan view of another example of the pressure-sensitive sensor relating to the first embodiment.

FIG. 9 is a schematic plan view of another example of the pressure-sensitive sensor 1 relating to the present embodiment. In this example, seams of the sewing threads 5 are dotted along both longitudinal side edges of the first-electrode cloths 3 and along both longitudinal side edges of the second-electrode cloths 4, and, it is regarded that the sewing threads 5 are sewn to enclose each of the areas V1 of intersection, in this specification. Further, in this example, the sewing threads 5 are sewn at outside positions of the four corners of each of the areas V1 of intersection. As shown in FIG. 9, the areas V1 of intersection between the first-electrode cloths 3 and the second-electrode cloths 4 are formed so as to have the matrix structure. With this structure, it is possible that the seams of the sewing threads 5 do not disturb stretch ability of the base cloths of the conductive cloth 2, the first-electrode cloths 3 and the second-electrode cloths 4 as much as possible. Note that, in some cases, the sewing threads 5 may be sewn at the four corners of each of the areas V1 of intersection, and the above described effects can be expected in this example, too.

Figure 10:
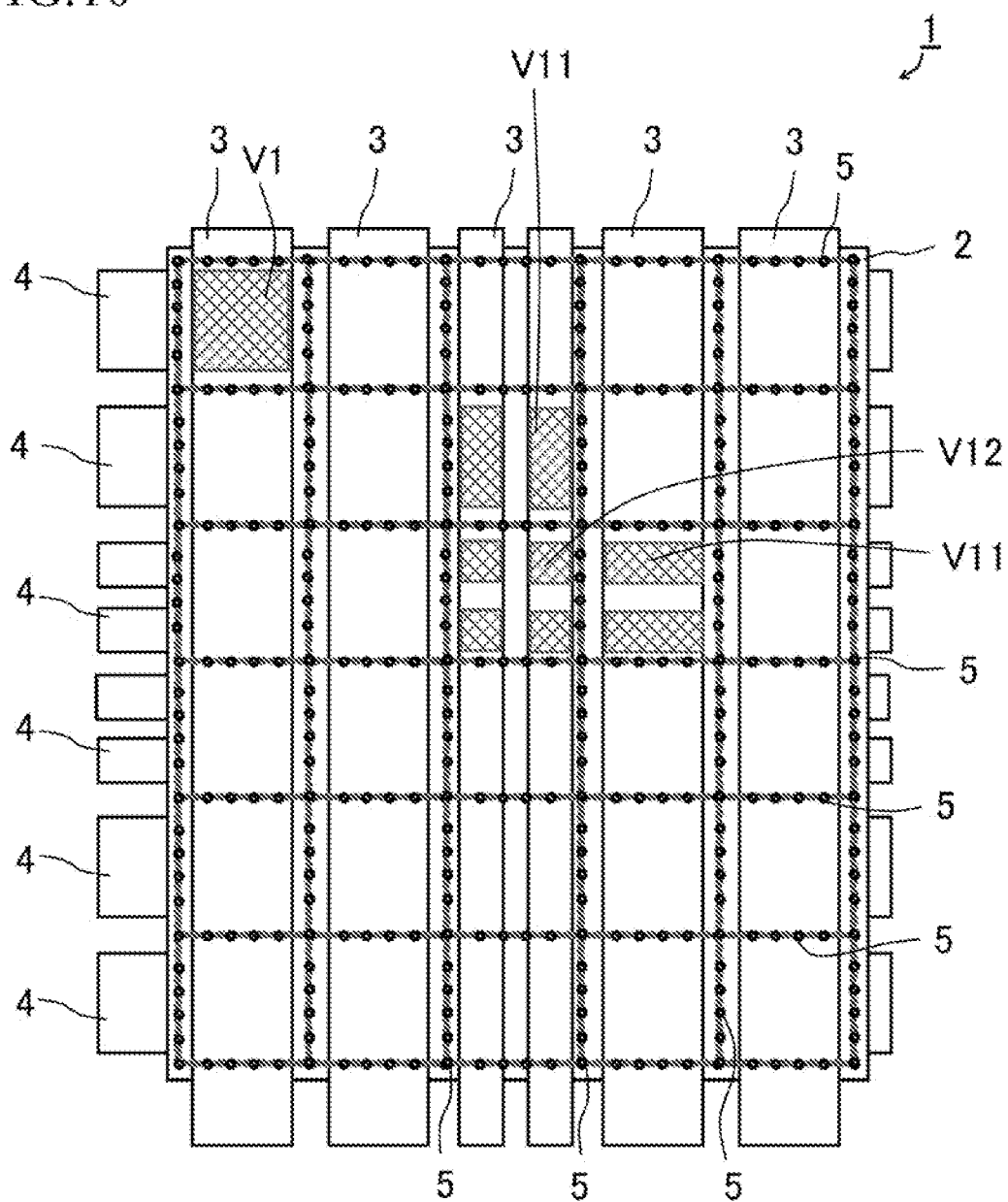
FIG. 10 is a schematic plan view of a further example of the pressure-sensitive sensor relating to the first embodiment.

FIG. 10 is a schematic plan view of a further example of the pressure-sensitive sensor 1 relating to the present embodiment. In the example shown in FIG. 10, transverse widths of the first-electrode cloths 3 and the second-electrode cloths 4 located in a center part of the pressure-sensitive sensor 1 are made narrower in plan view, so areas V11 of intersection, whose area is smaller than that of the area V1 of intersection, and areas V12, whose area is smaller than that of the areas V11 of intersection, are formed toward the center of the pressure-sensitive sensor 1. In this case too, the areas V1, V11 and V12 of intersection between the first-electrode cloths 3 and the second-electrode cloths 4 are formed so as to have the matrix structure. With this structure, resolution to external pressure can be heightened, toward the center of the pressure-sensitive sensor 1, by performing pressure conversion in proportion to areas of the areas V1, V11 and V12 of intersection. Note that, a region having high resolution to the external pressure is not limited to the center part of the pressure-sensitive sensor 1, and a plurality of said regions may be provided in desired parts.

Second Embodiment

Figure 11:
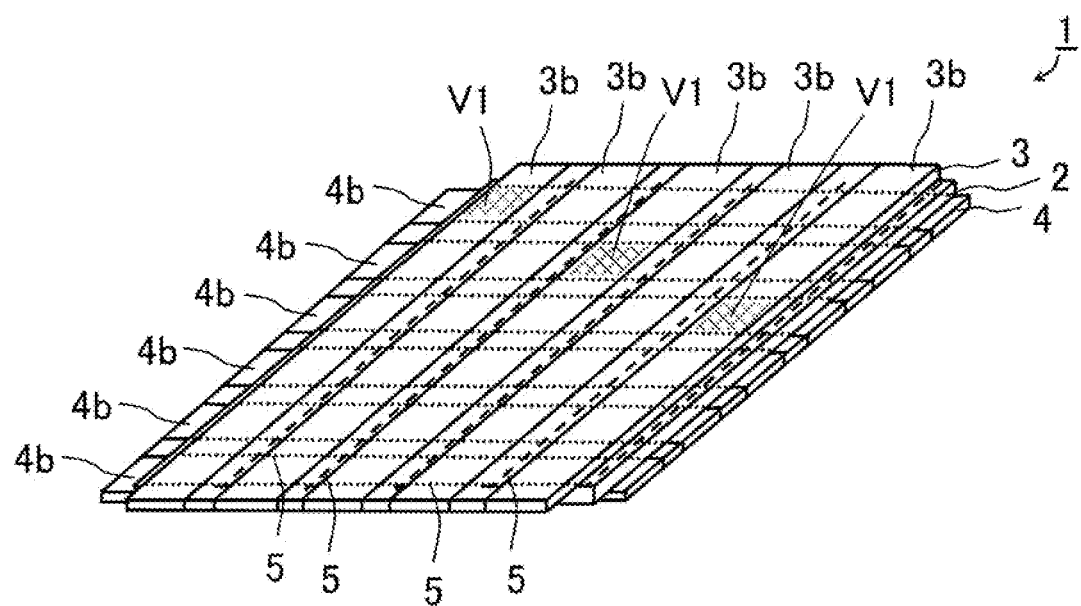
FIG. 11 is a schematic perspective view of an example of a pressure-sensitive sensor relating to a second embodiment of the present invention.
Figure 12:
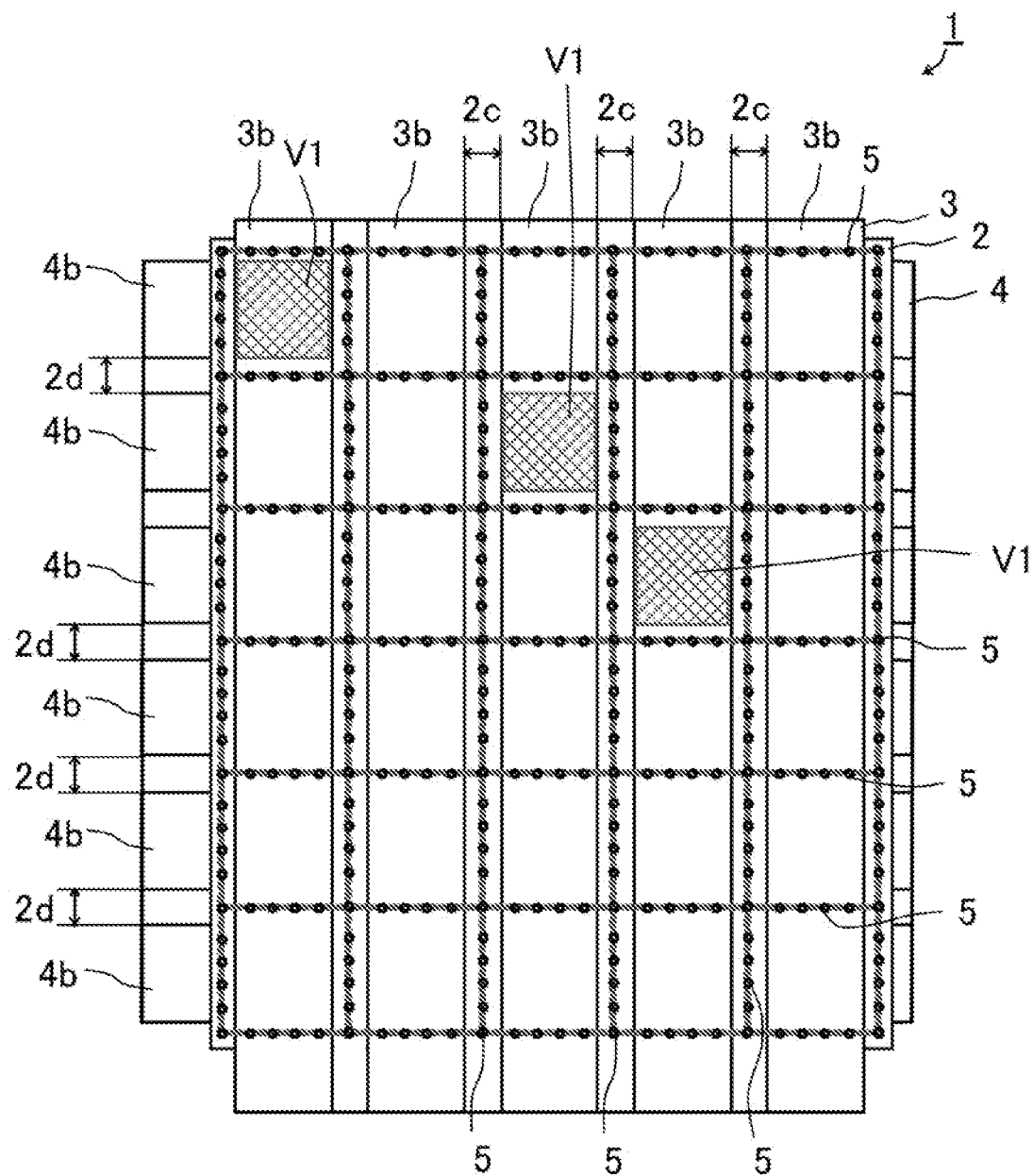
FIG. 12 is a schematic plan view of the pressure-sensitive sensor shown in FIG. 11.
Figure 13A:
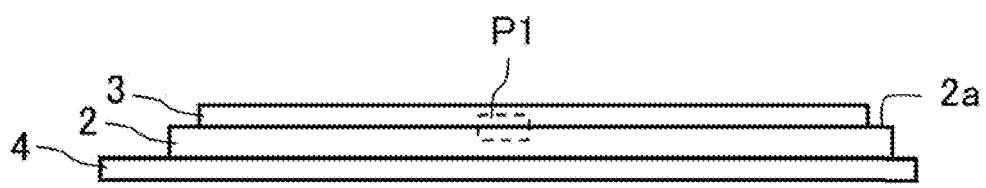
FIG. 13A is a schematic front view of the pressure-sensitive sensor shown in FIG. 11.
Figure 13A:
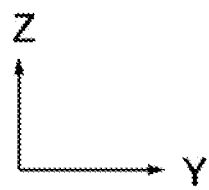
Figure 13B:
FIG. 13B is a schematic side view of the pressure-sensitive sensor shown in FIG. 11.
Figure 13B:
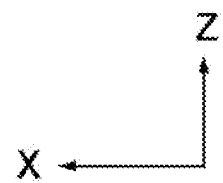

Successively, a second embodiment will be explained below. FIG. 11 is a schematic perspective view of an example of the pressure-sensitive sensor 1 relating to the second embodiment. FIG. 12 is a schematic plan view of the pressure-sensitive sensor 1 relating to the present embodiment. FIG. 13A is a schematic front view of the pressure-sensitive sensor 1 relating to the second embodiment, and FIG. 13B is a schematic side view of the pressure-sensitive sensor 1 relating to the second embodiment. For convenience of explanation, a cover cloth, signal wires, etc. are omitted in FIG. 11, etc. In the second embodiment, differences from the first embodiment will be mainly explained.

In the present embodiment, one first-electrode cloth 3 is provided on the first-surface 2a of the conductive cloth 2, and one second-electrode cloth 4 is provided on the second-surface 2b of the conductive cloth 2, a plurality of first-electrodes 3b are formed at the first-interval 2c on the first-electrode cloth 3, a plurality of second-electrodes 4b are formed at the second-interval 2d on the second-electrode cloth 4, the second-electrodes 4b intersect with the first-electrodes 3b, and the areas V1 of intersection between the first-electrodes 3b and the second-electrodes 4b are formed so as to have the matrix structure.

In the present embodiment, a width of the first-electrodes 3b in a transverse direction is wider than that of the first-intervals 2c in a transverse direction, and a width of the second-electrodes 4b in a transverse direction is wider than that of the second-intervals 2d in a transverse direction. With this structure, a leak current from an adjacent measurement position can be reduced, so that S/N ratio of detection signals, which are outputted in response to the pressurizing force, can be improved. As an example, the width of the first-electrodes 3b in the transverse direction and that of the second-electrodes 4b in the transverse direction are 10-100 [mm]. And, as an example, the width of the first-intervals 2c in the transverse direction and that of the second-interval 2d in the transverse direction are 1-10 [mm].

In the present embodiment, a thickness of the conductive cloth 2 is smaller than the width of the first-intervals 2c in the transverse direction, and the thickness of the conductive cloth 2 is smaller than the width of the second-intervals 2d in the transverse direction. With this structure, a leak current from an adjacent measurement position can be reduced, so that S/N ratio of detection signals, which are outputted in response to the pressurizing force, can be improved. For example, the thickness of the conductive cloth 2 is 0.3-0.6 [mm]. And, for example, the thicknesses of the first-electrode cloth 3 and the second-electrode cloth 4 are 0.2-0.6 [mm].

In some cases, the first-electrodes 3b are formed only on a surface of the first-electrode cloth 3 facing the first-surface 2a of the conductive cloth 2; in this case, a cost of an electrode material and the production cost can be reduced. And, in other some cases, the first-electrodes 3b are formed on the upper surface and the lower surface of the first-electrode cloth 3; in this case, any of the upper surface and the lower surface of the first-electrode cloth 3 may be stacked onto the conductive cloth 2, so that it is easy to produce. Further, in some cases, the first-electrodes 3b are made conductive in a thickness direction of the first-electrode cloth 3; in this case, reliability of conductivity of the electrodes can be improved.

In some cases, the second-electrodes 4b are formed only in a surface of the second-electrode cloth 4 facing the second-surface 2b of the conductive cloth 2; in this case, the cost of the electrode material and the production cost can be reduced. And, in other some cases, the second-electrodes 4b are formed on the upper surface and the lower surface of the second-electrode cloth 4; in this case, any of the upper surface and the lower surface of the second-electrode cloth 4 may be stacked onto the conductive cloth 2, so that it is easy to produce. Further, in some cases, the second-electrodes 4b are made conductive in a thickness direction of the second-electrode cloth 4, so that reliability of conductivity of the electrodes can be improved.

In the second embodiment, dimensions and numbers of the first-electrode cloth 3 and the second-electrode cloth 4 are different from those of the first embodiment. But, the sewing manners, sewing positions, the first-conductive particles 11, the second-conductive particles 12 and other structural elements may be similar to those of the first embodiment.

As a further example, the first-electrode cloth 3 and the second-electrode cloth 4 are composed of woven fabric. For example, warps are formed by alternately arranging a plurality of conductive threads, in which, for example, nylon cores are shelled by silver-plating, and a plurality of insulating threads, which are composed of, for example, nylon. And, wefts are formed by sequentially weaving a plurality of insulating threads, which are composed of, for example, nylon, so that the one first-electrode cloth 3, in which a plurality of the stripe-like electrodes are formed at a prescribed intervals, can be formed. Then, the second-electrode cloth 4, which is equivalent to the first-electrode cloth 3, is turned at 90° in the horizontal direction so as to form the matrically-arranged electrodes on the upper side and the lower side of the conductive cloth 2. Then, the first-electrode cloth 3, the conductive cloth 2 and the second-electrode cloth 4 are sewn to each other by sewing the parts not including the areas V1 of intersection with the sewing threads 5. With this structure, the pressure-sensitive sensor 1, whose freedom of the size is high and which is capable of utilizing flexibility of the cloths, can be provided.

Figure 14:
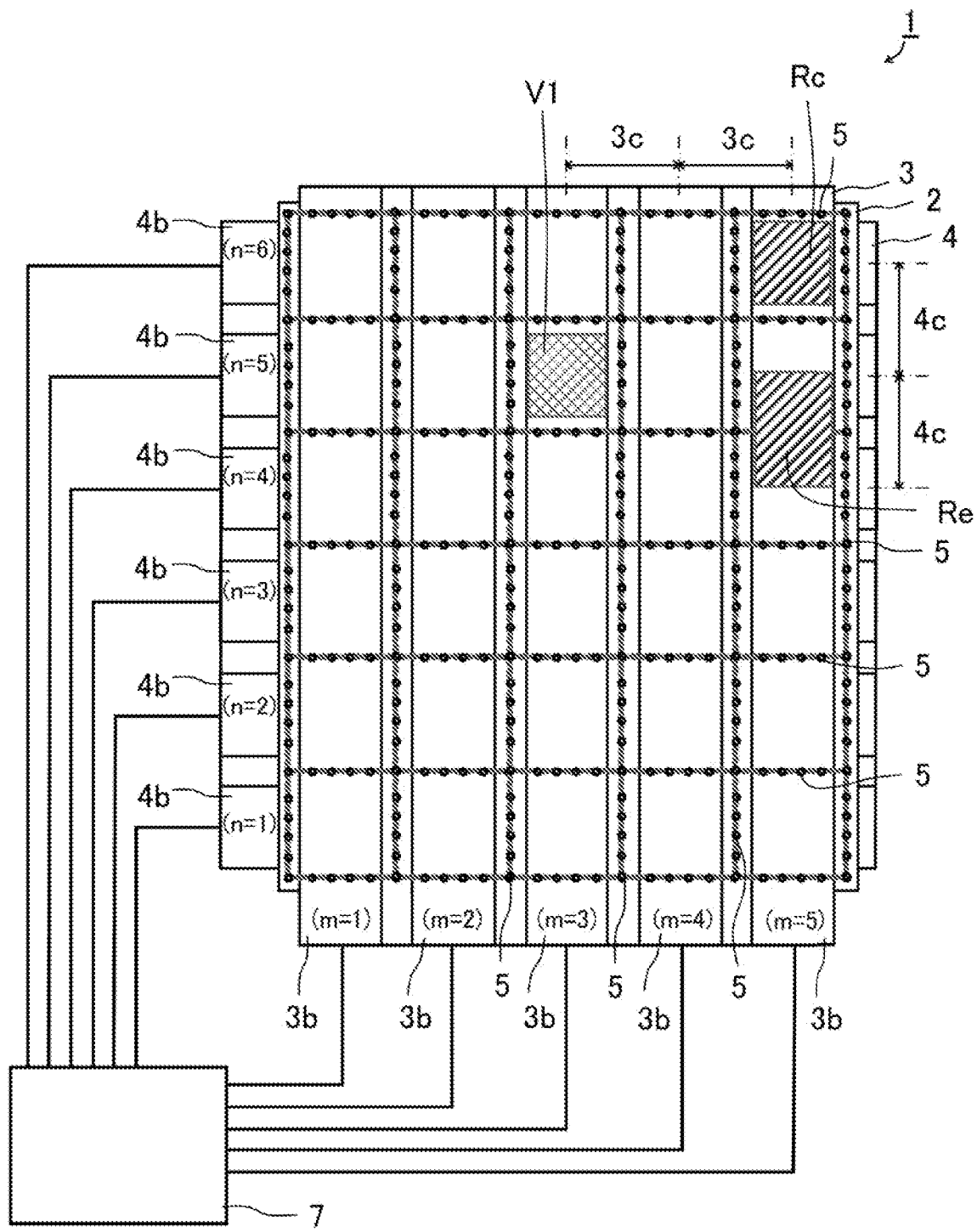
FIG. 14 is a schematic plan view of the example of the pressure-sensitive sensor relating to the second embodiment, in which the controller is connected.

FIG. 14 is a schematic plan view of an example of the pressure-sensitive sensor 1 relating to the second embodiment, in which the controller 7 is connected. The controller 7 has a CPU for controlling the signal wire switching circuit, the signal detector, the A/D converter, the semiconductor memories and the arithmetic circuit.

In the present embodiment, the one first-electrode cloth 3 is provided on the first-surface 2a of the conductive cloth 2 and the one second-electrode cloth 4 is provided on the second-surface 2b of the conductive cloth 2, the [m] number of first-electrodes 3b are formed at the first-intervals 2c on the first-electrode cloth 3, the [n] number of second-electrodes 4b are formed at the second-intervals 2d on the second-electrode cloth 4, the second-electrodes 4b intersect with the first-electrodes 3b, and the areas V1 of intersection between the first-electrodes 3b and the second-electrodes 4b are formed so as to have the matrix structure. Here, the numbers [m] and [n] are natural numbers 2 or more, and the numbers are, for example, m=5 and n=6 in the example shown in FIG. 14.

In the present embodiment, a resistance value Re [Ω], which is an average resistance value of the two areas V1 and V1 of intersection longitudinally adjacent to each other in the longitudinal direction, with respect to a resistance value Rc [Ω], which is an average resistance value of the areas V1 of intersection, in the thickness direction, in a state where an external force of 50 [mmHg] is applied, in the compaction direction, to move the first-electrode cloth 3 and the second-electrode cloth 4 close to each other, satisfies the above described Formula (1).

As shown in FIG. 14, in case that an electrode pitch 3c of the first-electrode cloth 3 in a row direction is equal to an electrode pitch 4c of the second-electrode cloth 4 in a column direction, the above described Formula (1) is satisfied.

On the other hand, in case that the electrode pitch 3c of the first-electrode cloth 3 and the electrode pitch 4c of the second-electrode cloth 4 are different from each other, the resistance value Re [Ω] is obtained from a weighted average value of an electrode resistance value R1 [Ω] of the first-electrode cloth 3, in which the electrode pitch is 3c in the row direction, and an electrode resistance value R2 [Ω] of the second-electrode cloth 4, in which the electrode pitch is 4c in the column direction, and it is calculated by the above described Formula (2). Resistance characteristics of the pressure-sensitive sensor are similar to those shown in FIGS. 15A, 15B, 16A and 16B.

Successively, a method of manufacturing the pressure-sensitive sensor 1 relating to the present invention will be explained below.

For example, the method of manufacturing the pressure-sensitive sensor 1 comprises: a step of forming the conductive cloth 2, in which a dispersion liquid of the first-conductive particles 11 composed of the conductive carbon black is applied to coat a first-base cloth; and a step of forming the electrode cloths, i.e., the first-electrode cloth 3 and the second-electrode cloth 4, in which a dispersion liquid of the second-conductive particles 12 having greater electrical conductivity than the first-conductive particles 11 is applied to coat second-base cloths. For example, the first-conductive particles 11 are composed of ketjenblack, and the second-conductive particles 12 are composed of a mixture of the conductive metal particles 12a and the conductive carbon black 12b; in the step of forming the electrode cloths, a mixture of the binder resin 13a whose rupture elongation is 100% or more and the first-conductive particles 11 is applied for coating; and, in the step of forming the conductive cloth, a mixture of binder resin 13b whose rupture elongation is 100% or more and the second-conductive particles 12 is applied for coating.

With the above described structure, the pressure-sensitive sensor can be easily manufactured, by the simple coating operations, without being limited by a size of a facility, e.g., plating facility. Further, the conductive carbon black can be obtained at a lower price than noble metals and conductive high polymer compounds, so that high productivity can be enabled with restraining the material cost.

After performing the step of forming the conductive cloth and the step of forming the electrode cloths, a sewing step, in which the second-electrode cloth 4 is sewn to the conductive cloth 2, with the non-conducting sewing threads 5, at positions in the first-clearances 3a between the first-electrode cloth 3 and the first-electrode cloth 3, and the first-electrode cloth 3 is sewn to the conductive cloth 2, with the non-conducting sewing threads 5, at positions in the second-clearances 4a between the second-electrode cloth 4 and the second-electrode cloth 4 so as to form the areas V1 of intersection having the matrix structure, is performed. In this sewing step, the sewing threads 5 are sewn by the sewing machine.

With the above described structure, the pressure-sensitive sensor 1 can be easily manufactured, by the simple sewing operations, without being restricted by a size of facility. Since areas of the electrode cloths to be sewn are smaller than that of the conductive cloth, high productivity can be enabled with restraining the material cost. Further, boundaries of the areas V1 of intersection for detecting pressurizing force are formed by the sewing operations, and the areas V1 of intersection are formed so as to have the matrix structure, so that accuracy of measuring the pressurizing force in each of the areas V1 of intersection can be improved.

The pressure-sensitive sensor 1 manufactured by the above described method can be applied to, for example, a bed, a mat for bed, a sheet, a cushion, a mat for chair, a health mat, a carpet, etc.

For example, by assembling the pressure-sensitive sensor 1 to a bed, a mat for bed or a sheet, forming decubitus ulcer can be prevented by measuring a sleeping posture of the human and inducing roll over with adjusting air pressure of an air mat. Further, by analyzing and calculating pressure waveforms of prescribed parts, the sensor is capable of measuring heartbeat or breath as a heartbeat sensor or a breathing sensor.

For example, by assembling the pressure-sensitive sensor 1 to a cushion or a mat for chair, a sitting posture can be measured and leaving seat can be detected, so that human actions can be known, and stiffness in shoulders or lower back pain can be prevented by adjusting pressure of an air cushion so as to correct the human posture.

For example, by assembling the pressure-sensitive sensor 1 to a health mat or a carpet, a walking posture of the human can be measured, and customizing shoes of the human can be performed by measuring foot pressures in a standing posture. Further, a human weight can be measured from contact resistance, and the sensor can be used for measuring human living habits, e.g., movement in a room.

Generally, in case of measuring pressure distribution in a char or a bed, the pressure-sensitive sensor 1 is capable of sufficiently measuring the pressurizing force within a range from 10 to 200 [mmHg]. Frequency of measurement by the pressure-sensitive sensor 1 is increased around 50 [mmHg].

Third Embodiment

Figure 18:
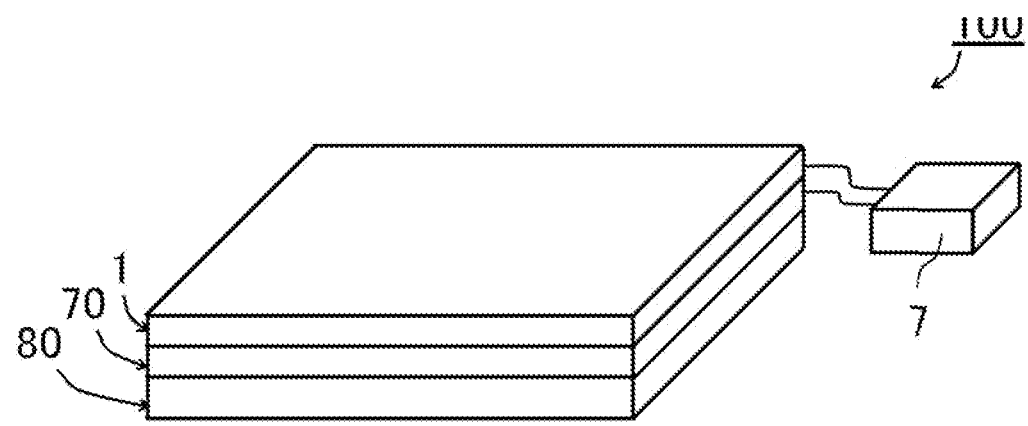
FIG. 18 is a schematic perspective view of an example of a mat system using the pressure-sensitive sensor relating to a third embodiment of the present invention.
Figure 19:
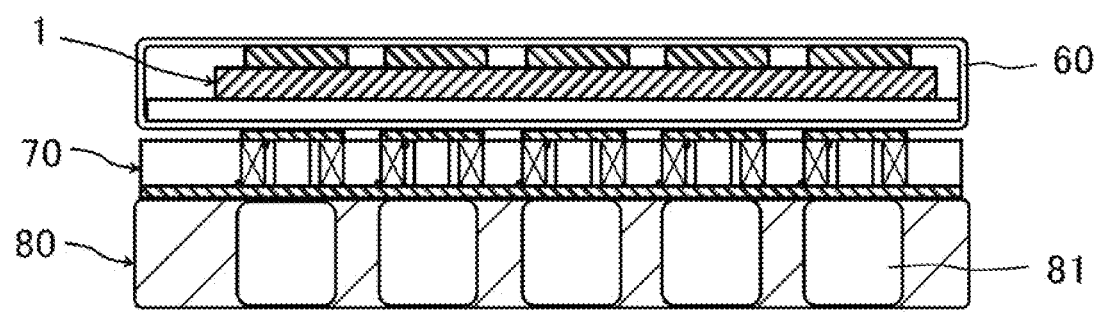
FIG. 19 is a schematic front sectional view of the mat system shown in FIG. 18.
Figure 19:
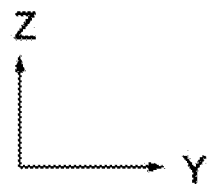

Successively, a third embodiment will be explained below. FIG. 18 is a schematic perspective view of a mat system 100 using the pressure-sensitive sensor. FIG. 19 is a schematic front sectional view of the mat system shown in FIG. 18. For convenience of explanation, a cover cloth, signal wires, etc. are omitted in FIG. 18. To easily explain positional relationships between parts of the mat system 100 using the pressure-sensitive sensor, the directions X, Y and Z are shown by arrows in the drawings. When actually using the mat system 100 using the pressure-sensitive sensor, a direction to be directed is not limited, and it may be directed in any directions without any problem. In the third embodiment, the pressure-sensitive sensor 1 relating to the above described first embodiment, the pressure-sensitive sensor 1 relating to the second embodiment, and the pressure-sensitive sensors 1 relating to a fourth embodiment and a fifth embodiment described later may be employed. Here, differences from the first embodiment and the second embodiment will be mainly explained.

The mat system 100 using the pressure-sensitive sensor comprises: a mat 80 being formed into a square shape and having a plurality of air cells 81; a magnetic field generating sheet 70 having a plurality of magnetic field generating parts which are matrically arranged on a body-side of the mat 80 (on the side indicated by the arrow Z shown in the drawings); the pressure-sensitive sensor 1 having a plurality of the pressure-sensitive parts which are matrically arranged on the body-side of the magnetic field generating sheet 70 (on the side indicated by the arrow Z shown in the drawings); and the controller 7 for controlling positions of the magnetic field generating parts to generate magnetic fields and timing of generating magnetic fields according to pressure distribution of the pressure-sensitive parts. Here, thicknesses of the magnetic field generating sheet 70 and the pressure-sensitive sensor 1 are smaller than that of the mat 80. With this structure, the mat system 100, which has flexibility with little uncomfortable feeling, can be provided. Further, the pressure-sensitive sensor 1 is covered with a cover cloth 60. As an example, the cover cloth 60 is composed of woven fabric or knitted fabric of, for example, cotton, nylon, acrylic or other known fibers, and a waterproof treatment or a water repellent treatment is performed on at least the body-side. With this structure, uncomfortable feeling for the human body can be reduced, and the pressure-sensitive sensor 1 can be prevented from invasion of water.

Figure 20:
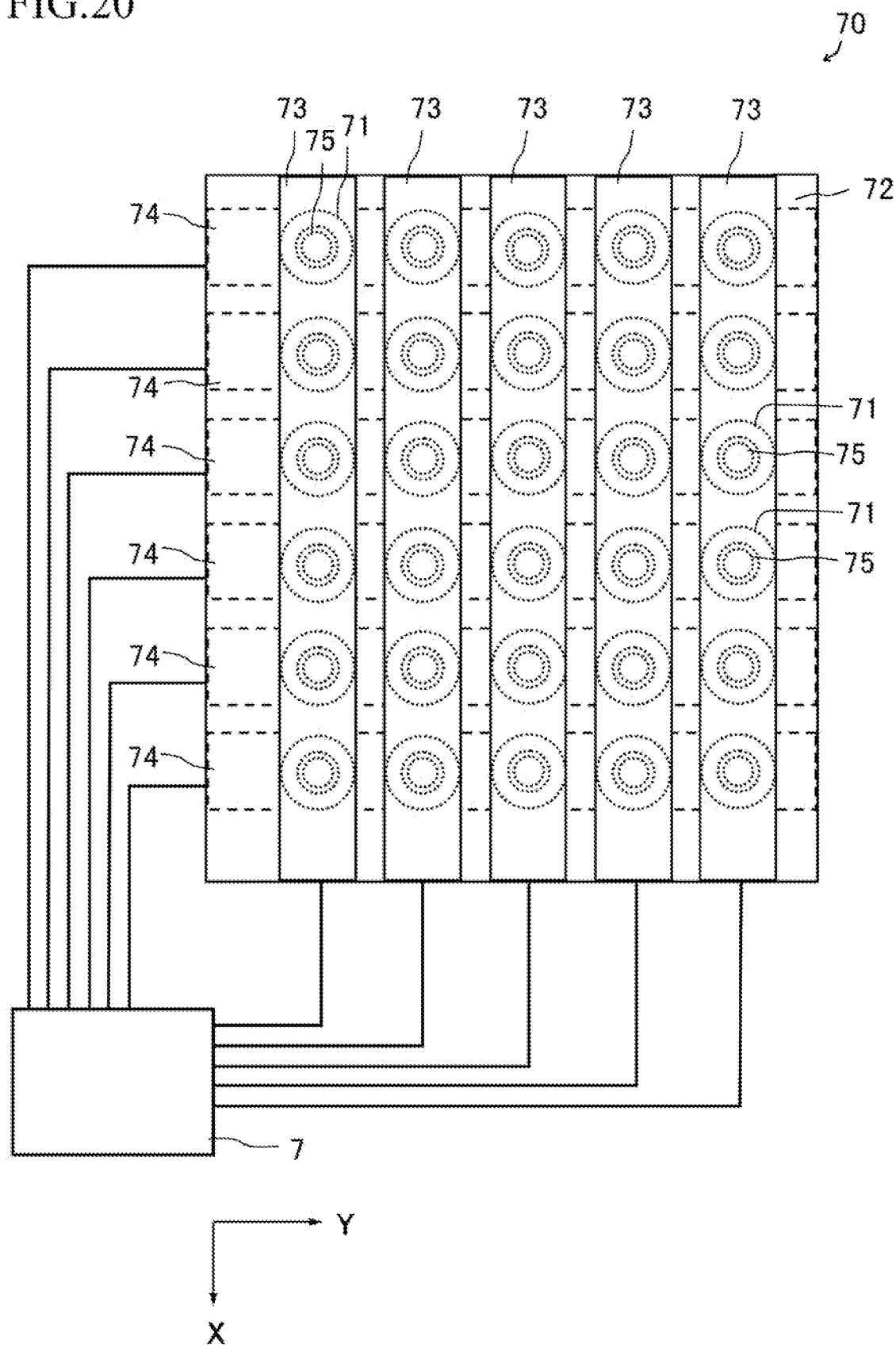
FIG. 20 is a schematic plan view of an example of a magnetic field generating sheet relating to the third embodiment, in which the controller is connected.
Figure 21:
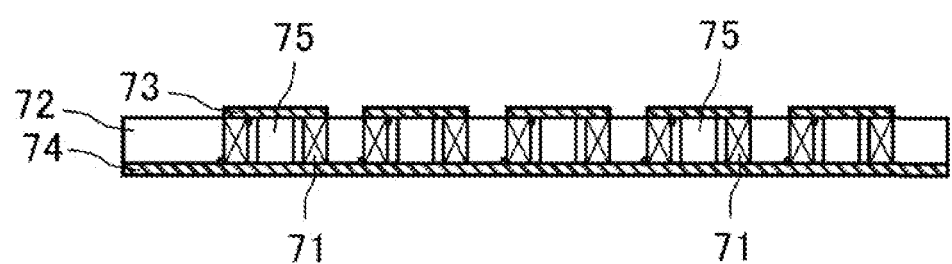
FIG. 21 is a schematic front sectional view of the magnetic field generating sheet shown in FIG. 20.

Next, the magnetic field generating sheet 70 will be explained below. FIG. 20 is a schematic plan view showing an example of the magnetic field generating sheet 70, in which the controller 7 is connected. FIG. 21 is a schematic front sectional view of the magnetic field generating sheet shown in FIG. 20. As an example, the magnetic field generating sheet 70 has a multilayer wiring substrate 72, in which base members are integrally layered and in which the base members are thermoplastic resin substrates, e.g., polyimide substrates, liquid crystal polymer substrates, on which copper foil patterns are formed, and electromagnetic coils 71 are formed by electrically connecting the copper foil patterns in a layering direction of the multilayer wiring substrate 72. Note that, in some other cases, the electromagnetic coils 71 are constituted by, for example, flat coils or voice coils in which insulating film copper wires are wound, and they are electrically connected to upper electrodes and lower electrodes as well as the pressure-sensitive sensor 1. In this case, the magnetic field generating sheet 70 can be manufactured, at a low price, by an existing facility.

Here, center parts of the electromagnetic coils 71 are hollow, and magnetic members 75 are provided therein. The magnetic members 75 are composed of a known permanent magnet, e.g., neodymium magnet, ferrite magnet, or a soft magnetic body, e.g., iron, cobalt, nickel, alloy thereof. In case that the magnetic members 75 are permanent magnets, magnetic poles are aligned in an axial direction. The electromagnetic coils 71 and the magnetic members 75 are formed so as to have the matrix structure and constitute a plurality of magnetic field generating parts. As an example, the matrix arrangement of the electromagnetic coils 71 and the magnetic members 75 correspond, one-on-one, to the matrix arrangement of the areas V1 of intersection of the pressure-sensitive sensor 1. Note that, in another case, for example, no magnetic members 75 are provided. In this case, the magnetic field generating sheet 70, which is thin and has superior flexibility, can be easily manufactured.

The controller 7 controls positions of the electromagnetic coils 71 (the magnetic field generating parts) to generate magnetic fields and timing of generating magnetic fields according to pressure distribution of the areas V1 of intersection (the pressure-sensitive parts) of the pressure-sensitive sensor 1.

In the present embodiment, the electromagnetic coils 71 capable of generating magnetic fields are located at the positions corresponding to the areas V1 of intersection of the pressure-sensitive sensor 1 for measuring pressure distribution, and the controller 7 excites the electromagnetic coils 71 in order of high pressure value parts of the pressure-sensitive sensor 1, so that moving magnetic fields are generated in the mat 80. By generating the moving magnetic fields in the mat system 100 using the pressure-sensitive sensor, promoting a flow of blood including hemoglobin, in the human body, can be enabled.

Generally, a blood flowing speed in the human body is 0.3 [mm/second] in capillary vessels and 400 [mm/second] in main arteries, and a large number of capillary vessels exist in parts of skin close to a surface of the mat system 100 using the pressure-sensitive sensor. Therefore, the moving speed of the moving magnetic fields is preferably controlled from 0.3 [mm/second] to 30 [mm/second].

In case that, for example, a pitch of the areas V1 of intersection of the pressure-sensitive sensor 1 is 30 [mm] and a pitch of the electromagnetic coils 71 is 30 [mm], it is prefer to switch excitation of the electromagnetic coils 71 at a frequency of 0.1 [Hz]±0.05 [Hz]. In this case, the electromagnetic coils 71 may be sequentially excited one by one, or a plurality of adjacent electromagnetic coils 71 may be simultaneously excited. For example, setting of the controller 7 may be adjusted according to user's inclination.

In case that the magnetic members 75 are provided to the center parts of the electromagnetic coils 71, movable concavities and convexities can be formed on a surface of the mat system 100 using the pressure-sensitive sensor which contacts the human body, so that promotion of the blood flow can be enabled.

Further, by adding the mat 80 as air cell mats, changing the posture can be induced, and blood flow stagnation in a head, shoulders, a lower back, heels, etc., at each of which pressure will be increased by holding same posture (same bodily position) for a long time, can be improved.

Fourth Embodiment

Figure 22:
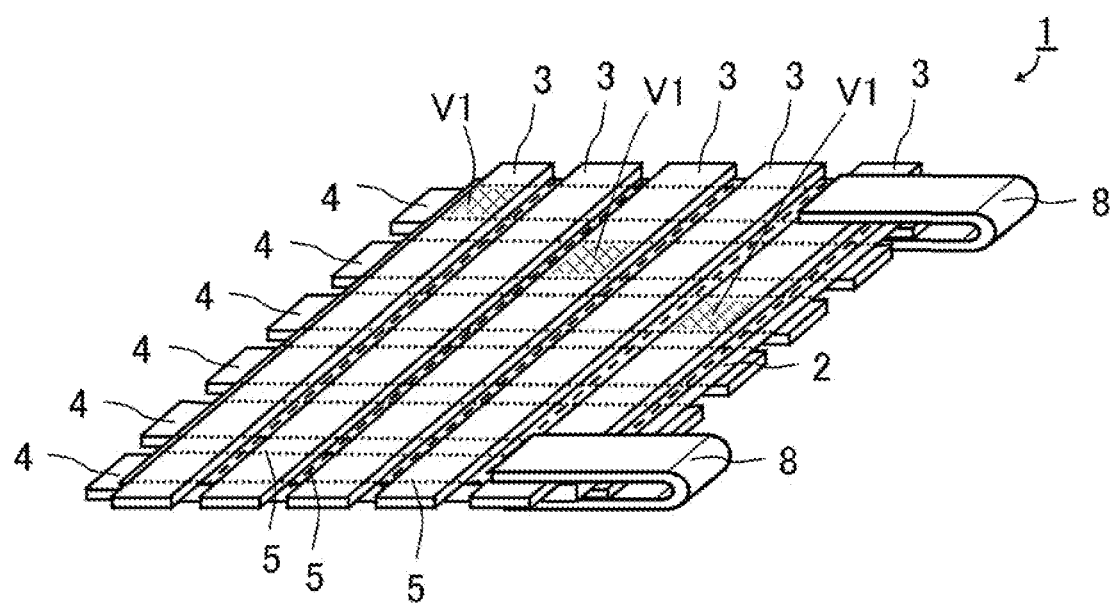
FIG. 22 is a schematic perspective view of an example of the pressure-sensitive sensor relating to a fourth embodiment of the present invention.
Figure 22:
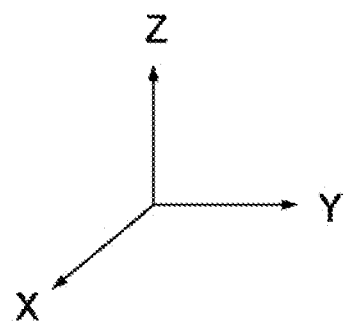
Figure 23:
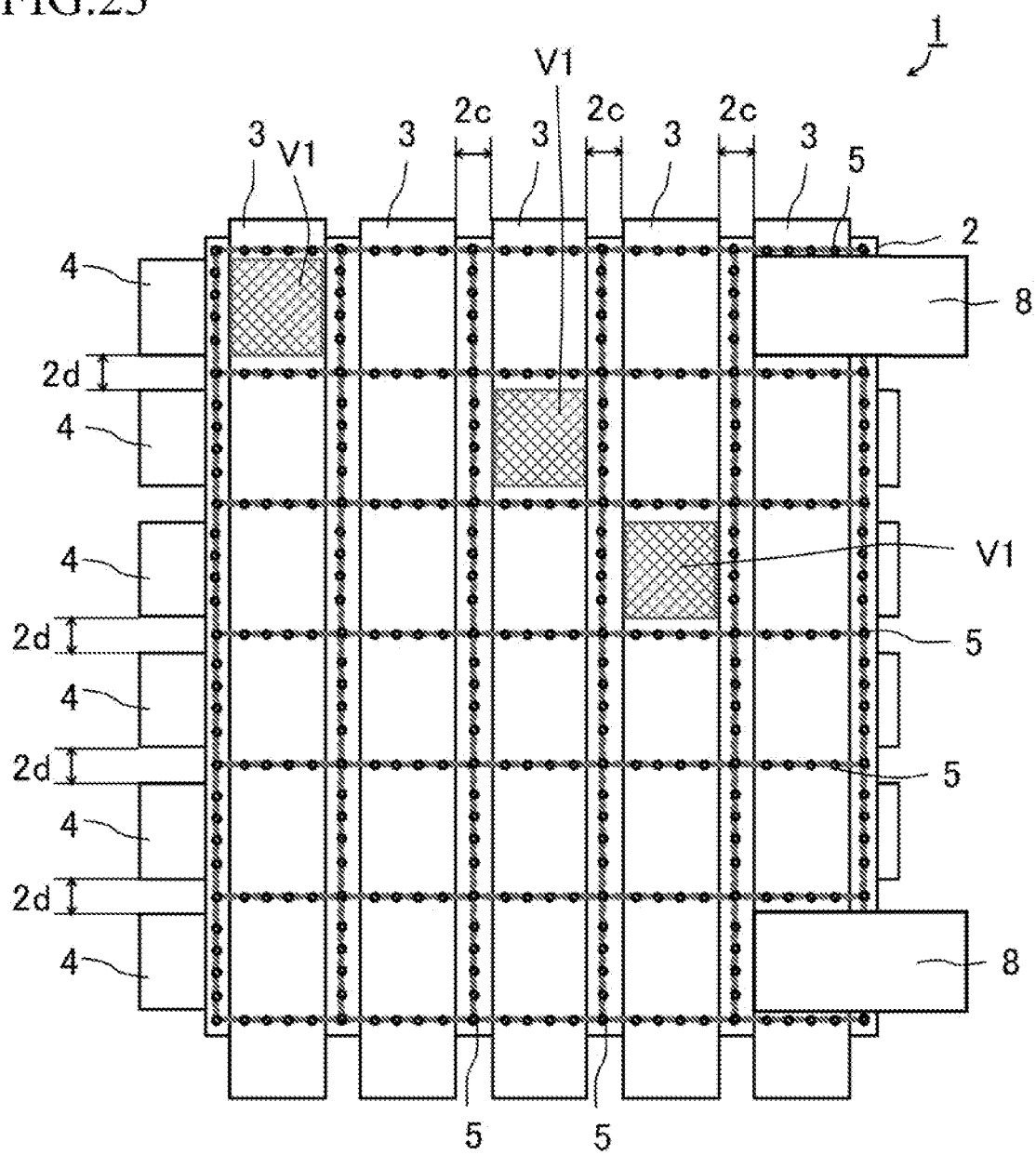
FIG. 23 is a schematic plan view of the pressure-sensitive sensor shown in FIG. 22.

Successively, a fourth embodiment will be explained below. FIG. 22 is a schematic perspective view of the pressure-sensitive sensor 1 relating to the fourth embodiment. FIG. 23 is a schematic plan view of the sensor shown in FIG. 22. For convenience of explanation, a cover cloth, signal wires, etc. are omitted in FIG. 22, etc. In the fourth embodiment, differences from the first embodiment and the second embodiment will be mainly explained.

As shown in FIGS. 22 and 23, the pressure-containing members 8 are provided to the areas V1 of intersection located at two corners, on one end-side, out of the areas V1 of intersection at four corners, and correction or calibration of pressure distribution at positions, at which no pressure-containing members 8 are provided, is performed according to sensed pressure values at the positions of the pressure-containing members 8.

Figure 24A:
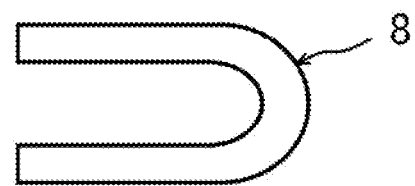
FIG. 24A is a schematic side view of an example of a pressure-containing member of the pressure-sensitive sensor relating to the fourth embodiment.
Figure 24B:
FIG. 24B is a schematic side view of another example of the pressure-containing member of the pressure-sensitive sensor relating to the fourth embodiment.

As shown in FIG. 24A, the pressure-containing member 8 is a U-shaped clip composed of a constantly elastic material. In another case, the pressure-containing member 8 is composed of, for example, a clothespin-like clip having a coil spring 81 as shown in FIG. 24B. The pressure-containing member 8 is composed of, for example, insulating resin, e.g., polybutylene terephthalate (PBT), acrylonitrile-butadiene-styrene copolymer resin (ABS), polyacetal (POM), polymethacrylic acid methyl resin (PMMA), liquid crystal polymer (LCP), insulating-coated constantly elastic metals, e.g., stainless steel, nickel alloy, elinvar alloy, glass, other known constantly elastic materials.

In the present embodiment, correcting or calibrating abnormalities, e.g., deformation of the pressure-sensitive parts caused by compression permanent set, contact resistances between the electrodes and the pressure-sensitive parts, variation of use environment such as temperature, humidity, water-invasion to the pressure-sensitive parts, can be easily performed, with maintaining and improving reproducibility of the sensed value, by treating the sensed pressure value of the pressure-containing members 8 as standards. Since the pressure-containing members 8 are provided to positions displaced from a center of a contact part which contacts the human body, biological information can be measured, without difficulty, even by the thick pressure-containing members 8, too. Note that, in other cases, the pressure-containing member 8 is provided to the area V1 of intersection located at one corner out of the areas V1 of intersection at the four corners, the pressure-containing members 8 are provided to the areas V1 of intersection located at three corners out of the areas V1 of intersection at the four corners, and the pressure-containing members 8 are provided to the areas V1 of intersection located at four corners out of the areas V1 of intersection at the four corners.

Fifth Embodiment

Figure 25:
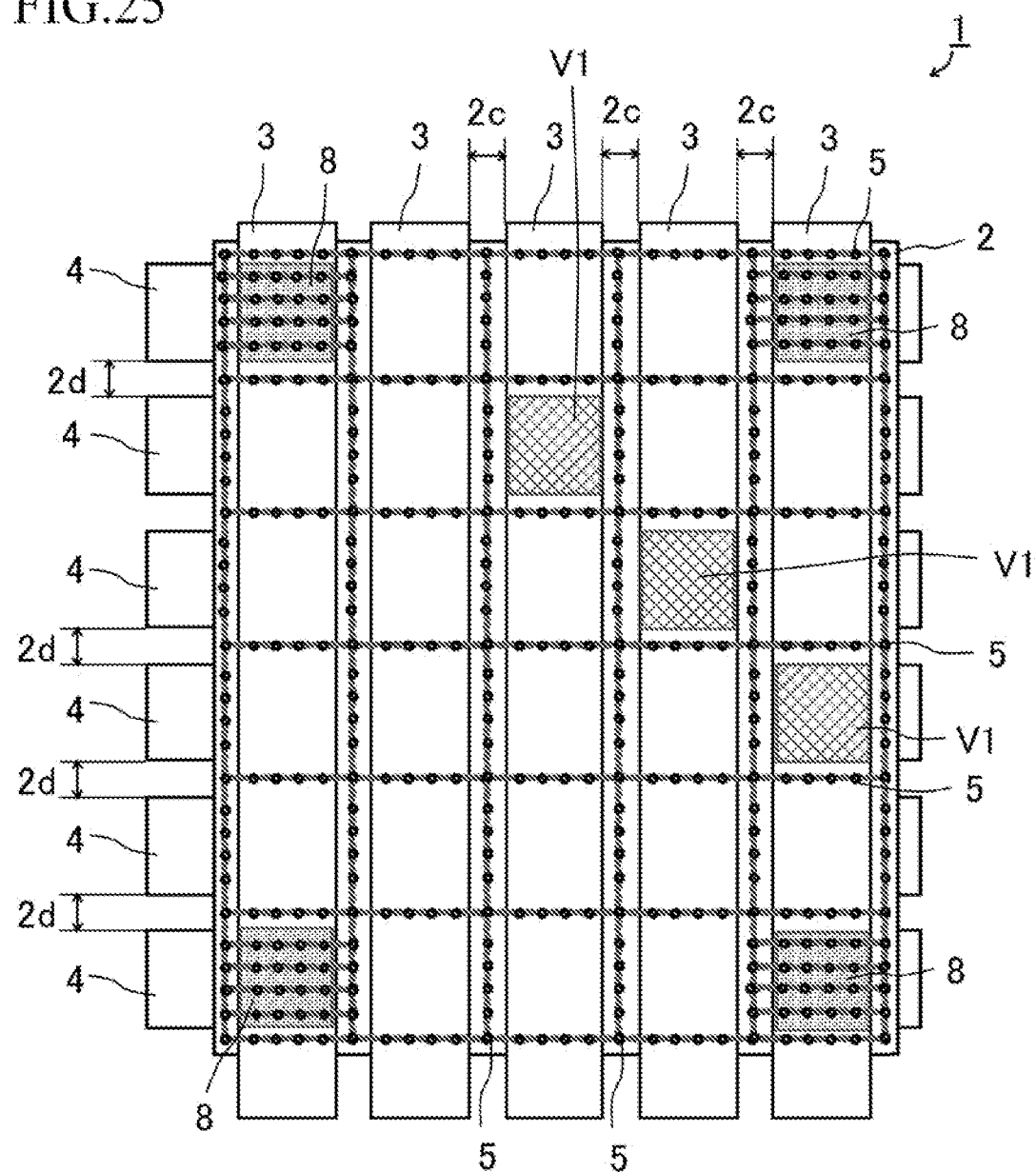
FIG. 25 is a schematic perspective view of an example of the pressure-sensitive sensor relating to a fifth embodiment of the present invention.

Successively, the pressure-sensitive sensor 1 relating to the fifth embodiment will be explained below. FIG. 25 is a schematic plan view of an example of the pressure-sensitive sensor 1 relating to the fifth embodiment. For convenience of explanation, a cover cloth, signal wires, etc. are omitted in FIG. 25, etc. In the fifth embodiment, differences from the fourth embodiment will be mainly explained.

In the present example, seams of the sewing threads 5 are formed at a plurality of positions in the areas V1 of intersection located at two corners, on one end-side, out of the areas V1 of intersection at four corners, and the pressure-containing members 8, which hold the first-electrode cloths 3 and the second-electrode cloths 4 at a prescribed pressure in the compaction direction to move them close to each other, are formed by the sewing threads 5. With this structure, the pressure-sensitive sensor 1 can be made thin, and the material cost can be reduced. Note that, in other cases, the pressure-containing member 8 is provided to the area V1 of intersection located at one corner out of the areas V1 of intersection at the four corners, the pressure-containing members 8 are provided to the areas V1 of intersection located at three corners out of the areas V1 of intersection at the four corners, and the pressure-containing members 8 are provided to the areas V1 of intersection located at four corners out of the areas V1 of intersection at the four corners.

Figure 26:
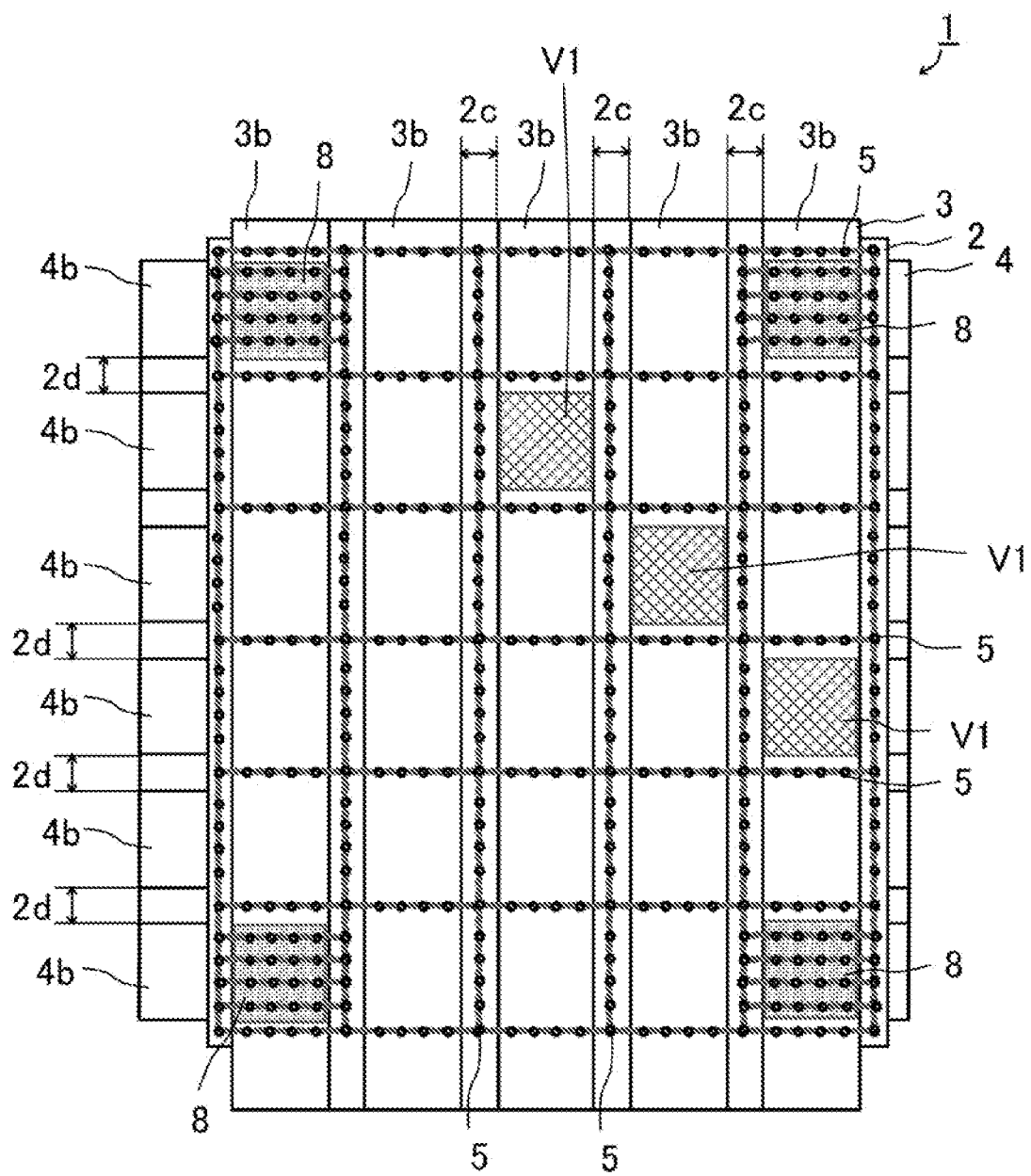
FIG. 26 is a schematic perspective view of another example of the pressure-sensitive sensor relating to the fifth embodiment of the present invention.

FIG. 26 is a schematic plan view of another example of the pressure-sensitive sensor 1 relating to the fifth embodiment. In this example, the pressure-containing members 8 are provided to the areas V1 of intersection located at the four corners, and the pressure-containing members 8, which hold the first-electrode cloth 3 and the second-electrode cloth 4 at a prescribed pressure in the compaction direction to move them close to each other, are formed by the sewing threads 5.

PRACTICAL EXAMPLE

The conductive cloth 2 was formed by applying a mixture liquid, which included fine particles of ketjenblack as the first-conductive particles 11, urethane resin as binder, and water, to coat nylon knitted fabric which acted as the first-base cloth. The first-electrode cloths 3 and the second-electrode cloths 4 were formed by applying a mixture liquid, which included a mixture of fine silver particles 12a and conductive carbon black 12b as the second-conductive particles 12, urethane resin as binder and water, to coat nylon knitted fabrics which acted as the second-base cloths. Then, by performing the lock stitching with the sewing machine, the second-electrode cloths 4 were sewn to the conductive cloth 2 with the nylon sewing threads 5, the first-electrode cloths 3 were sewn to the conductive cloth 2 with the nylon sewing threads 5, and the areas V1 of intersection between the first-electrode cloths 3 and the second-electrode cloths 4 were formed so as to have the matrix structure, so that the prototype pressure-sensitive sensor 1 was manufactured.

Figure 17:
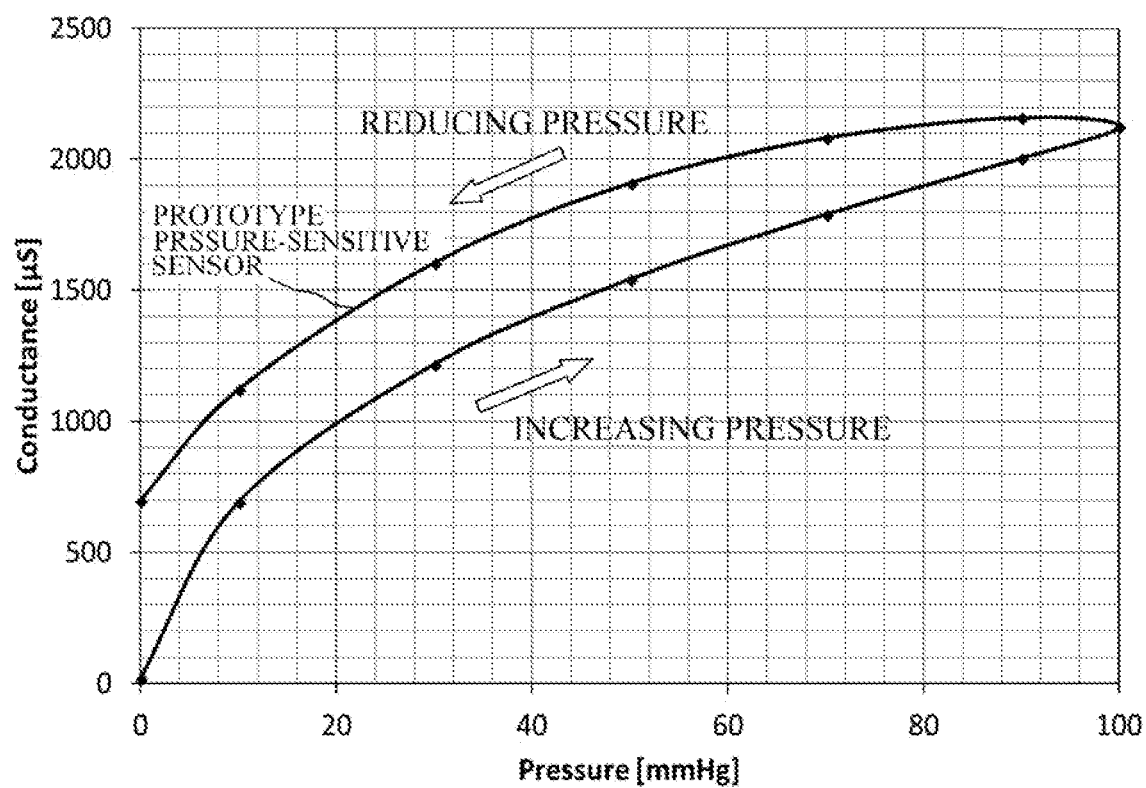
FIG. 17 is a pressure-sensitive-characteristic graph showing a relationship between pressure and conductance in an area of intersection of the pressure-sensitive sensor.

FIG. 17 is a pressure-sensitive-characteristic graph showing a relationship between pressure applied by an airbag and conductance in the area V1 of intersection (second row, second column) of the prototype pressure-sensitive sensor 1. A vertical axis of the graph indicates conductance [μS], and a horizontal axis of the graph indicates pressure [mmHg].

As shown in FIG. 17, conductance is increased (resistance value is reduced) by increasing pressure, and conductance is reduced (resistance value is increased) by reducing pressure. In the nature of restorative forces of fibers, the graph formed a hysteresis curve. Note that, in case of continuously applying same pressure, conductance was gradually increased (resistance value was reduced) in response to elapse of time (not shown).

As shown in FIG. 17, the curve of conductance while increasing pressure and that while reducing pressure were similarly inclined, so it was known that the measurement can be performed with high reproducibility.

In some cases, the shape and the size of the above described pressure-sensitive sensor 1 will be suitably changed according to specifications, etc. of known beds, mats for beds, sheets, cushions, mats for chairs, health mats, carpets. The present invention is not limited to the above described embodiments, and various modifications may be allowed without deviating the scope of the invention.

What is claimed is:

1. A pressure-sensitive sensor comprising: a conductive cloth; a first-electrode cloth being provided on a first-surface of the conductive cloth; and a second-electrode cloth being provided on a second-surface of the conductive cloth, wherein a plurality of first-electrodes are formed on the first-electrode cloth and arranged at a first-interval, a plurality of second-electrodes are formed on the second-electrode cloth and arranged at a second-interval, the second-electrodes are arranged in a direction intersecting that of the first-electrodes, and areas of intersection between the first-electrode electrodes and the second-electrodes are formed so as to have a matrix structure, or a pressure-sensitive sensor comprising: a conductive cloth; a plurality of first-electrode cloths being arranged at a first-interval on a first-surface of the conductive cloth; and a plurality of second-conductive cloths being arranged at a second-interval on a second-surface of the conductive cloth in a direction intersecting that of the first-electrode cloths, wherein areas of intersection between the first-electrode cloths and the second-electrode cloths are formed so as to have a matrix structure, wherein first-conductive particles are applied to coat the conductive cloth, second-conductive particles having greater electrical conductivity than the first-conductive particles are applied to coat the first-electrode cloth or cloths and the second-electrode cloth or cloths, and the first-conductive particles are composed of conductive carbon black.

2. The pressure-sensitive sensor according to claim 1, wherein a mixture of the first-conductive particles and binder resin whose rupture elongation is 100% or more is applied to coat the conductive cloth, a mixture of the second-conductive particles and binder resin whose rupture elongation is 100% or more is applied to coat the first-electrode cloth or cloths, and a mixture of the second-conductive particles and binder resin whose rupture elongation is 100% or more is applied to coat the second-electrode cloth or cloths.

3. The pressure-sensitive sensor according to claim 1, wherein all of the conductive cloth, the first-electrode cloth or cloths and the second-electrode cloth or cloths are composed of woven fabric, or all of the conductive cloth, the first-electrode cloth or cloths and the second-electrode cloth or cloths are composed of knitted fabric.

4. The pressure-sensitive sensor according to claim 1, further comprising sewing threads, wherein the first-electrode cloth or cloths are sewn to the conductive cloth with the sewing threads, and the second-electrode cloth or cloths are sewn to the conductive cloth with the sewing threads.

5. The pressure-sensitive sensor according to claim 4, wherein the sewing threads are sewn at outside positions of four corners of the area of intersection or at the positions of the four corners thereof.

6. The pressure-sensitive sensor according to claim 5, wherein the parts at which the sewing threads are sewn are concaved by tension of the sewing threads.

7. The pressure-sensitive sensor according to claim 6, wherein the sewing threads are non-conducting sewing threads and sewn by a sewing machine.

8. The pressure-sensitive sensor according to claim 4, wherein all of the conductive cloth, the first-electrode cloth or cloths and the second-electrode cloth or cloths are composed of woven fabric, or all of the conductive cloth, the first-electrode cloth or cloths and the second-electrode cloth or cloths are composed of knitted fabric.

9. The pressure-sensitive sensor according to claim 1, wherein a resistance value Re, which is an average resistance value of the two areas of intersection longitudinally adjacent to each other in the longitudinal direction, with respect to, an average resistance value Rc of the areas of intersection in a thickness direction, in a state where an external force of 50 mmHg is applied in a compaction direction to move the [m] number of first-electrode cloths and the [n] number of second-electrode cloths to each other, satisfies the following Formula (1)

Formula (1)

$$1 < Re < (Rc/(m+n)) \quad (1).$$

10. The pressure-sensitive sensor according to claim 1, wherein a pressure-containing member for containing prescribed pressure in a compaction direction is provided to at least one of the areas of intersection.

11. The pressure-sensitive sensor according to claim 10, wherein the pressure-containing member is provided to at least one of the areas of intersection located at four corners, and correcting or calibrating pressure distribution at a position different from that of the pressure-containing member is performed on the basis of a sensed pressure value at the position of the pressure-containing member.

12. The pressure-sensitive sensor according to claim 11, wherein a plurality of the pressure-containing members are provided to a plurality of the areas of intersection, and pressures of the pressure-containing members at respective positions are different from each other.

13. The pressure-sensitive sensor according to claim 10, wherein the pressure-containing member has an elastic part capable of applying prescribed pressure in the compaction direction.

14. A method of manufacturing a pressure-sensitive sensor comprising: a conductive cloth; a first-electrode cloth being provided on a first-surface of the conductive cloth; and a second-electrode cloth being provided on a second-surface of the conductive cloth, wherein a plurality of first-electrodes are formed on the first-electrode cloth and arranged at a first-interval, a plurality of second-electrodes are formed on the second-electrode cloth and arranged at a second-interval, the second-electrodes are arranged in a direction intersecting that of the first-electrodes, and areas of intersection between the first-electrode electrodes and the second-electrodes are formed so as to have a matrix structure,
or a method of manufacturing a pressure-sensitive sensor comprising: a conductive cloth; a plurality of first-electrode cloths being arranged at a first-interval on a first-surface of the conductive cloth; and a plurality of second-conductive cloths being arranged at a second-interval on a second-surface of the conductive cloth in a direction intersecting that of the first-electrode cloths, wherein areas of intersection between the first-electrode cloths and second-electrode cloths are formed so as to have a matrix structure, said method comprising:

a step of forming the conductive cloth by applying a dispersion liquid of first-conductive particles to coat a first-base cloth so as to form the conductive cloth; and a step of forming the electrode cloths by applying a dispersion liquid of second-conductive particles having greater electrical conductivity than the first-conductive particles to coat second-base cloths so as to form the first-electrode cloth or cloths and the second-electrode cloth or cloths, wherein the first-conductive particles are composed of conductive carbon black.

* * * * *